(12) United States Patent
Sheehan et al.

(10) Patent No.: US 7,427,632 B2
(45) Date of Patent: Sep. 23, 2008

(54) FACTOR XA INHIBITORS

(75) Inventors: Scott Martin Sheehan, Carmel, IN (US); Brian Morgan Watson, Carmel, IN (US); John Walter Liebeschuetz, Macclesfield (GB)

(73) Assignee: Eli Lilly and Company, Indianapolis, IN (US)

( * ) Notice: Subject to any disclaimer, the term of this patent is extended or adjusted under 35 U.S.C. 154(b) by 516 days.

(21) Appl. No.: 10/539,372

(22) PCT Filed: Dec. 22, 2003

(86) PCT No.: PCT/US03/39101

§ 371 (c)(1),
(2), (4) Date: Jun. 16, 2005

(87) PCT Pub. No.: WO2004/060872

PCT Pub. Date: Jul. 22, 2004

(65) Prior Publication Data

US 2006/0052606 A1    Mar. 9, 2006

Related U.S. Application Data

(60) Provisional application No. 60/436,625, filed on Dec. 30, 2002.

(51) Int. Cl.
| | |
|---|---|
| *A61K 31/445* | (2006.01) |
| *A61K 31/454* | (2006.01) |
| *A61K 31/4545* | (2006.01) |
| *C07D 209/42* | (2006.01) |
| *C07D 333/60* | (2006.01) |
| *C07D 401/12* | (2006.01) |
| *C07D 295/13* | (2006.01) |
| *C07D 295/15* | (2006.01) |
| *C07D 295/088* | (2006.01) |
| *A61K 31/495* | (2006.01) |
| *A61K 31/496* | (2006.01) |

(52) U.S. Cl. ............ 514/318; 514/323; 514/326; 514/331; 514/254.09; 546/193; 546/194; 546/201; 546/233; 546/234; 546/213; 546/232; 544/360; 544/373; 544/379; 544/380; 544/400; 544/403

(58) Field of Classification Search .............. None
See application file for complete search history.

(56) References Cited

U.S. PATENT DOCUMENTS

| 6,855,715 B1 | 2/2005 | Liebeschuetz et al. |
| 6,900,196 B2 | 5/2005 | Liebeschuetz et al. |

FOREIGN PATENT DOCUMENTS

| WO | 535256 | * 4/1993 |
| WO | WO 99/11657 | 3/1999 |
| WO | WO 99/11658 | 3/1999 |
| WO | WO 00/39111 | 7/2000 |
| WO | WO 00/76971 | 12/2000 |
| WO | WO 01/96303 | 12/2001 |

OTHER PUBLICATIONS

Mashkovsky et al. Khimiko-Farmatsevticheskii Zhurnal,vol. 25,pp. 27-31 (1995) (English translation).*
Jones, S D, et al., Bioorg. Med. Chem. Lett., vol. 11, 2001, pp. 733-736.

* cited by examiner

*Primary Examiner*—Emily Bernhardt
(74) *Attorney, Agent, or Firm*—Thomas E. Jackson

(57) ABSTRACT

Compounds of formula (I)

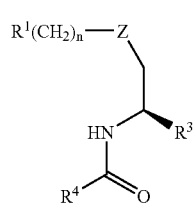

(I)

in which $R^1$, n, Z, $R^3$ and $R^4$ have any of the meanings given in the specification, are inhibitors of the serine protease Factor Xa and are useful in the treatment of thrombotic disorders.

21 Claims, No Drawings

FACTOR XA INHIBITORS

This application claims the benefit of U.S. provisional patent application Ser. No. 60/436,625 filed Dec. 30, 2002, the disclosure of which is incorporated by reference herein.

The present invention relates to compounds useful as pharmaceuticals, to pharmaceutical compositions comprising the compounds, to a process for preparing the compounds, to intermediates useful in the preparation of the compounds, and to use of the compounds as pharmaceuticals.

Cardiovascular disease continues to present a major worldwide health problem, and is a common cause of serious illness and death.

One line of investigation being pursued by researchers in the search for new treatments for cardiovascular disease is based upon the hypothesis that an inhibitor of the serine protease, Factor Xa, may be useful as an anticoagulant agent in the treatment of thrombotic disease.

Inhibitors of Factor Xa are known. For example, WO 01/96303 discloses compounds containing an aromatic group, a glycine residue bearing a cyclic group, and a cyclic amine linked to the glycine residue through an amide group.

Surprisingly, it has now been found that by replacing the amide group in compounds of WO 01/96303 with an alkylene, oxaalkylene or azaalkylene group, compounds may be obtained that are selective Factor Xa inhibitors and have particularly advantageous properties.

Accordingly, the present invention provides a compound of formula (I)

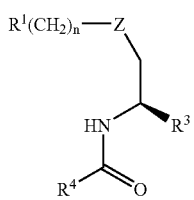

in which:

$R^1$ represents pyrrolidin-1-yl, piperidin-1-yl or a group of formula

in which X represents CH or N;

$R^2$ represents a hydrogen atom or a (1-6C)alkyl, (3-6C)cycloalkyl, fluoro(1-4C)alkyl, fluoro(2-4C)alkanoyl, hydroxy(2-4C)alkyl or pyridyl group;

n represents 1, 2 or 3;

Z represents $CH_2$, O or $NR^5$, in which $R^5$ represents a hydrogen atom or a (1-4C)alkyl group, provided that when $R^1$ represents pyrrolidin-1-yl, piperidin-1-yl or a group of formula

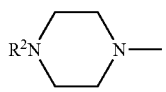

and Z represents O or $NR^5$, then n represents 2 or 3;

$R^3$ represents:

(i) phenyl which is unsubstituted or substituted by methylenedioxy or by a substituent selected from halogen, (1-4C)alkyl, hydroxy, (1-4C)alkoxy, trifluoromethyl, difluoromethoxy, trifluoromethoxy, (1-4C)alkylthio, (1-4C)alkylsulfinyl, (1-4C)alkylsulfonyl, carboxy, aminocarbonyl, amino, (2-4C)alkanoylamino, aminosulfonyl, (1-4C)alkylaminosulfonyl, nitro, phenyl, phenoxy, benzyloxy and pyridyl;

(ii) pyridyl, pyrimidyl or pyridazinyl, which is unsubstituted or substituted by a halogen atom;

(iii) furyl, thienyl, imidazolyl, thiazolyl, isothiazolyl, oxazolyl, isoxazolyl, thiadiazolyl, each of which is unsubstituted or substituted by (1-4C)alkyl or amino;

(iv) naphthyl, benzofuryl, benzothienyl, quinolyl or isoquinolyl;

(v) (3-6C)cycloalkyl; or (vi) (1-4C)alkyl, which is unsubstituted or substituted by hydroxy, (1-4C)alkoxy, phenoxy, carboxy, aminocarbonyl, aminosulfonyl, (1-4C)alkylthio, phenylthio, pyridylthio, amino, (1-4C)alkylamino, di(1-4C)alkylamino, piperidin-1-yl, morpholino, trifluoromethyl, phenyl, imidazolyl, pyridyl, (3-6C)cycloalkyl, oxa(4-6C)cycloalkyl, or aza(4-6C)cycloalkyl (which may bear an N-(1-4C)alkyl substituent); and $R^4$ is selected from

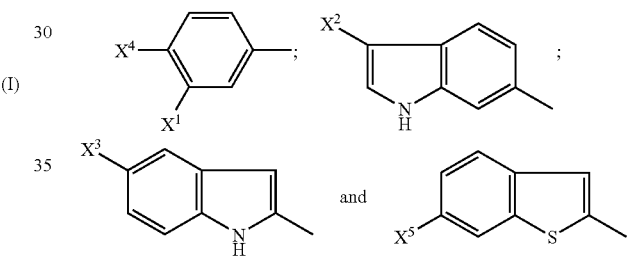

in which $X^1$ represents a hydrogen atom, a halogen atom or an amino group;

$X^2$ represents a hydrogen atom, a methyl group, a chlorine atom or a bromine atom;

$X^3$ represents a hydrogen atom, a methyl group or a halogen atom;

$X^4$ represents a chlorine atom, a methoxy group or a methyl group; and $X^5$ represents a hydrogen atom, a halogen atom or a methyl group;

or a pharmaceutically acceptable salt thereof.

Compounds of formula (I) have been found to be potent and selective inhibitors of the serine protease, Factor Xa, to have good anticoagulant activity in human plasma, to have good plasma exposure upon oral administration to mammals, and to possess particularly advantageous pharmacological profiles of activity.

It will be appreciated that compounds of formula (I) excluded by the proviso would be expected to be chemically unstable.

It will also be appreciated that the compounds of formula (I) contain a center of asymmetry that has the (R)-configuration when Z is O or $NR^5$ and the (S)-configuration when Z is $CH_2$. The compounds may therefore exist and be isolated in a mixture with the corresponding (S)- or (R)-isomer respectively, such as a racemic mixture, or separately. Preferably the compounds are isolated substantially free of the respective isomers.

It will further be appreciated that the compounds of formula (I) or their pharmaceutically acceptable salts may be isolated in the form of solvates, and accordingly that any such solvate is included within the scope of the present invention.

Examples of pharmaceutically acceptable salts include hydrochloride salts.

$R^1$ preferably represents a group of formula $$R^2N\diagup\diagdown X-$$

in which X represents CH or N.

X preferably represents CH.

$R^2$ preferably represents a (1-6C)alkyl, (3-6C)cycloalkyl, fluoro(1-4C)alkyl, fluoro(2-4C)alkanoyl, hydroxy(2-4C)alkyl or pyridyl group.

Compounds of formula (I) in which R2 represents hydrogen have generally been found to exhibit lower potency as Factor Xa inhibitors than the corresponding substituted compounds. However, as described hereinafter, they are useful as intermediates in the preparation of the substituted compounds.

Examples of particular values for $R^2$ are methyl, ethyl, isopropyl, cyclopropyl, cyclopentyl, 2-fluoroethyl, 2,2,2-trifluoroethyl, trifluoroacetyl, 2-hydroxyethyl and pyrid-4-yl group.

Preferably $R^2$ represents a isopropyl, cyclopropyl, cyclopentyl or pyrid-4-yl group.

Preferably n represents 1 or 2.

More preferably n represents 1.

In one group of compounds of formula (I), Z represents $CH_2$.

In another group of compounds of formula (I), Z represents O. Compounds within this group have been found to have particularly good plasma exposure upon oral administration to mammals.

In yet another group of compounds of formula (I), Z represents $NR^5$. Compounds belonging to this group have been found to have particularly good metabolic stability. Within this group, $R^5$ preferably represent a hydrogen atom. Compounds in which $R^5$ preferably represent a hydrogen atom have been found to possess particularly high potency as Factor Xa inhibitors, compared with compounds in which the nitrogen atom is substituted with $R^5$.

Examples of particular values for $R^3$ are:—

(i) phenyl, 2,3-methylenedioxyphenyl, 2-fluorophenyl, 4-fluorophenyl, 2-chlorophenyl, 2-methylphenyl, 2-methoxyphenyl, 2-trifluoromethylphenyl, 2-difluoromethoxyphenyl, 4-carboxyphenyl or 4-aminocarbonylphenyl;

(ii) pyrid-2-yl or pyrid-4-yl;

(iii) fur-2-yl, fur-3-yl, thien-2-yl, thien-3-yl, imidazol-2-yl, thiazol-2-yl, thiazol-4-yl, 2-methylthiazol-4-yl or 2-aminothiazol-4-yl;

(iv) naphth-1-yl, naphth-2-yl, benzofuryl, benzothienyl, quinolin-4-yl or quinolin-8-yl;

(v) cyclopropyl, cyclobutyl, cyclopentyl or cyclohexyl; or (vi) methyl, ethyl, propyl, isopropyl, butyl, 2-methylpropyl, hydroxymethyl, 1-hydroxyethyl, methoxymethyl, 1-methoxyethyl, methylthiomethyl, 2-methylthioethyl, prop-2-ylthiomethyl, N,N-dimethylaminomethyl, phenylthiomethyl, pyrid-2-ylthiomethyl, carboxymethyl, 2-carboxyethyl, aminocarbonylmethyl, 2-aminocarbonylethyl, morpholinomethyl, 2,2,2-trifluoroethyl, benzyl, pyrid-2-ylmethyl, pyrid-3-ylmethyl, pyrid-4-ylmethyl, imidazol-1-ylmethyl, imidazol-2-ylmethyl, 3-methylimidazol-4-ylmethyl, cyclohexyl-4-ylmethyl, tetrahydropyran-4-ylmethyl, piperidin-1-ylmethyl or 1-methylpiperidin-4-ylmethyl.

Preferably $R^3$ represents phenyl, 2-fluorophenyl or 2-chlorophenyl.

More preferably $R^3$ represents phenyl.

$X^3$ preferably represents a hydrogen atom, a chlorine atom or a methyl group.

$X^4$ preferably represents a chlorine atom.

$X^5$ preferably represents a chlorine atom.

Examples of particular values for $R^4$ are 4-chlorophenyl, 4-methoxyphenyl, indol-6-yl, 3-methylindol-6-yl, 3-chloroindol-6-yl, 5-chloroindol-2-yl or 6-chlorobenzo[b]thiophen-2-yl.

Preferably $R^4$ is 4-methoxyphenyl, indol-6-yl or 5-chloroindol-2-yl.

Particular mention may be made of:

3-Chloro-N-[(R)-1-phenyl-2-[1-(4-pyridinyl)piperidin-4-ylmethoxy]ethyl]-1H-indole-6-carboxamide; 3-Chloro-N-{(R)-2-[(1-isopropylpiperidin-4-ylmethyl)amino]-1-phenylethyl}-1H-indole-6-carboxamide; and pharmaceutically acceptable salts thereof.

According to another aspect, the present invention provides a process for preparing a compound of formula (I) or a pharmaceutically acceptable salt thereof as defined hereinabove, which comprises (a) reacting a compound of formula (II)

$$R^1(CH_2)_n-Z \diagdown_{H_2N}\diagdown R^3 \qquad (II)$$

or a salt thereof, with a compound of formula (III)

$$HOOC-R^4 \qquad (III)$$

or a reactive derivative thereof;

(b) for a compound of formula (I) in which $R^2$ represents a (1-6C)alkyl, (3-6C)cycloalkyl, fluoro(1-4C)alkyl, fluoro(2-4C)alkanoyl or hydroxy(2-4C)alkyl group, reacting a corresponding compound of formula (I) in which $R^2$ represents a hydrogen atom, or a salt thereof, with an alkylating or acylating agent;

(c) for a compound of formula (I) in which Z represents NH, deprotecting a compound of formula $$R^1(CH_2)_n-NR^6 \diagdown_{HN}\diagdown R^3 \qquad (IV)$$
$$\quad\quad\quad R^4\diagdown_O$$

in which $R^6$ represents an amino protecting group; or (d) for a compound of formula (I) in which $R^2$ represents a hydrogen atom, deprotecting a compound of formula (I) in which $R^2$ represents a protecting group;

followed, if a pharmaceutically acceptable salt is desired, by forming a pharmaceutically acceptable salt.

The reaction between the compound of formula (II) with the compound of formula (III) may conveniently be performed employing reagents and reaction conditions conventionally used for the formation of an amide bond. The reaction is conveniently carried out in the presence of a benzotriazole-based reagent such as 1-hydroxybenzotriazole, 1-hydroxy-7-azabenzotriazole or O-benzotriazol-1-yl-N,N,N',N'-tetramethyluronium hexafluorophosphate, and a carbodiimide-based dehydrating agent such as dicyclohexylcarbodiimide or 1-(3-dimethylaminopropyl)-3-ethylcarbodiimide, in an inert organic solvent such as dimethylformamide and/or methylene chloride. The reaction is conveniently conducted at a temperature of from 0 to 50° C., preferably at ambient temperature. If a salt of a compound of formula (II) is used, the reaction is conveniently performed in the additional presence of a base such as triethylamine. Other suitable reagents and solvents are known in the art, for example an acid halide, such as p-anisoyl chloride, or an acid anhydride, in the presence of a base, such as triethylamine or pyridine.

The alkylation of a compound of formula (I) in which $R^2$ represents a hydrogen atom may be performed using a conventional alkylating agent, such as by reductive alkylation using an aldehyde or ketone as the alkylating agent, or by reaction with a compound of formula $R^2$-$Z^a$ in which $Z^a$ represents a leaving atom or group, for example a chlorine or bromine atom or an organosulfonyloxy group, such as trifluoromethanesulfonyloxy.

Thus, the compound of formula (I) may be reacted with an aldehyde or ketone in the presence of a reducing agent, such as sodium cyanoborohydride or sodium triacetoxyborohydride. The reaction is conveniently performed at a temperature in the range of from 0 to 100° C. Suitable solvents include alkanols, such as methanol, halogenated hydrocarbons, such as methylene chloride, and carboxylic acids, such as acetic acid.

The alkylation of a compound of formula (I) in which $R^2$ represents a hydrogen atom with a compound of formula $R^2$-$Z^a$ is conveniently performed in the presence of a base, such as potassium carbonate. Convenient solvents include sulfoxides, such as dimethylsulfoxide and alkanols, such as ethanol. The reaction is conveniently performed at a temperature in the range of from 0 to 100° C.

The acylation of a compound of formula (I) in which $R^2$ represents a hydrogen atom may be performed using a method analogous to process step (a) as described hereinabove.

In processes (c) and (d), the protecting group represented by $R^6$ and $R^2$ respectively may be any suitable amino protecting group. The protection of amino groups is described in McOmie, Protecting Groups in Organic Chemistry, Plenum Press, NY, 1973, and Greene and Wuts, Protecting Groups in Organic Synthesis, 2nd. Ed., John Wiley & Sons, NY, 1991. Examples of amino protecting groups include acyl groups, such as groups of formula $R^8CO$ in which $R^8$ represents $C_{1-6}$ alkoxy, aryl-$C_{1-6}$ alkoxy (such as phenyl-$C_{1-6}$ alkoxy or fluorenyl-$C_{1-6}$ alkoxy), or $C_{3-10}$ cycloalkoxy, wherein a phenyl group may be optionally substituted, for example by one or two of halogen, $C_1$-$C_4$ alkyl and $C_1$-$C_4$ alkoxy.

Preferred amino protecting groups include benzyloxycarbonyl (CBz), t-butoxycarbonyl (Boc) and 9-fluorenylmethoxycarbonyl (fmoc).

The compounds of formula (II) in which Z represents O may be prepared by reacting a compound of formula (V)

with a compound of formula (VI)

$R^1(CH_2)_n$-$Z^b$ (VI)

in which $Z^b$ represents a leaving atom or group, such as a methanesulfonyloxy group, or a protected derivative thereof in which any $R^2$ present in $R^1$ represents an amino protecting group, such as t-butoxycarbonyl, in the presence of a strong base, such as sodium hydride.

The compounds of formula (II) in which Z represents $CH_2$ may be prepared by reducing an oxime compound of formula (VII)

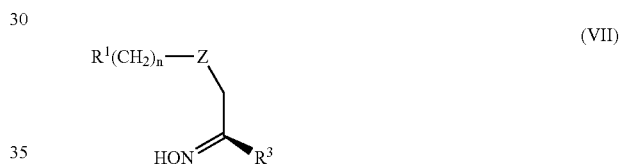

for example using hydrogen in the presence of palladium on carbon.

The compounds of formula (VII) may be prepared by reacting a compound of formula (VIII)

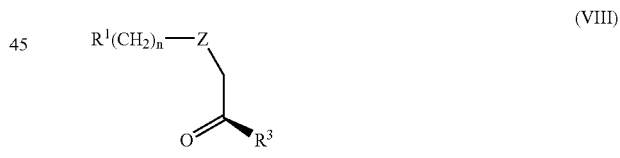

with hydroxylamine hydrochloride.

The compounds of formula (II) in which Z represents $NR^5$ may be prepared by deprotecting a compound of formula (IX)

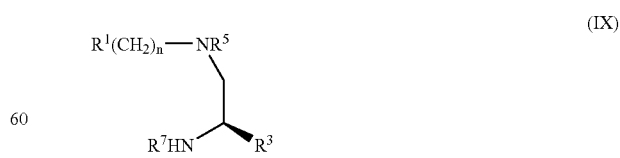

in which $R^7$ represents an amino protecting group, such as t-butoxycarbonyl.

The compounds of formula (IX) in which $R^5$ represents hydrogen may be alkylated to afford compounds of formula (IX) in which $R^5$ represents (1-4C)alkyl, or may be protected on the nitrogen with a protecting group $R^6$ to afford a compound of formula (IX) in which $R^5$ represents $R^6$, for use in the preparation of compounds of formula (IV) as described hereinafter.

The compounds of formula (IX) in which $R^5$ represents hydrogen may be prepared by reducing a compound of formula (X)

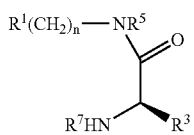

(X)

The compounds of formula (X) may be prepared by coupling a protected amino acid of formula (XI)

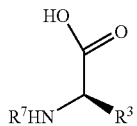

(XI)

with an amine of formula (XII)

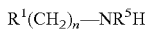

(XII)

using a procedure analogous to process (a) described hereinabove

The compounds of formula (III) are well known.

The compounds of formula (IV) may be prepared by reacting a compound of formula (IX) in which $R^5$ represents $R^6$ with a compound of formula (III) or a reactive derivative thereof, as described for process step (a) hereinabove.

Certain of the intermediates described herein, for example the compounds of formulae (II) and (IV), are believed to be novel and accordingly are provided as further aspects of the invention.

The compounds of the invention may be administered by any convenient route, e.g. into the gastrointestinal tract (e.g. rectally or orally), the nose, lungs, musculature or vasculature or transdermally. The compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. If parenteral administration is desired, the compositions will be sterile and in a solution or suspension form suitable for injection or infusion. Such compositions form a further aspect of the invention.

According to another aspect, the present invention provides a pharmaceutical composition, which comprises a compound of formula (I) or a pharmaceutically acceptable salt thereof, as defined hereinabove, together with a pharmaceutically acceptable diluent or carrier.

According to another aspect, the present invention provides the compound of formula (I) or a pharmaceutically acceptable salt thereof, for use in therapy.

According to another aspect, the present invention provides the use of the compound of formula (I) or a pharmaceutically acceptable salt thereof, for the manufacture of a medicament for the treatment of a thrombotic disorder.

According to another aspect, the present invention provides a method of treating a thrombotic disorder in a subject requiring treatment, which comprises administering an effective amount of a compound of formula (I) or a pharmaceutically acceptable salt thereof.

The subject may be a human or a non-human animal, such as a non-human mammal, for example a cat, dog, horse, cow or sheep.

The thrombotic disorder may be, for example, venous thrombosis, pulmonary embolism, arterial thrombosis, myocardial ischaemia, myocardial infarction or cerebral thrombosis. The compounds may also be used in accordance with the method of the invention in the treatment of acute vessel closure associated with thrombolytic therapy and restenosis, for example after transluminal coronary angioplasty or bypass grafting of the coronary or peripheral arteries, and in the maintenance of vascular access patency in long term hemodialysis patients.

The dosage of the compounds of formula (I) will depend upon the nature and severity of the condition being treated, the administration route and the size and species of the subject. In general, quantities in the range of from 0.01 to 100 μM/kg bodyweight will be administered.

As used herein, the term "treatment" includes prophylactic use. The term "effective amount" refers to the amount of the compound of formula (I) that is effective to reduce or inhibit the development of the symptoms of the thrombotic disorder being treated.

The compound according to the invention may be administered alone or in combination with an anticoagulant having a different mode of action or with a thrombolytic agent.

The following Examples illustrate the invention.

Abbreviations used follow IUPAC-IUB nomenclature. Additional abbreviations are aq., aqueous; equiv, (molar) equivalent; HPLC, high-performance liquid chromatography; rpHPLC, reverse phase HPLC; SCX, strong cation exchange resin; THF, tetrahydrofuran; HOAc, acetic acid; DMSO, dimethyl sulfoxide (perdeuterated if for NMR); EtOAc, ethyl acetate; EtOH, ethanol; DMF, dimethylformamide; DCM, dichloromethane; HOAT, 1-hydroxy-7-azabenzotriazole; HOBT, 1-hydroxy benzotriazole, HBTU, O-benzotriazol-1-yl-N,N,N',N'-tetramethyluronium hexafluorophosphate; DCC, dicyclohexylcarbodiimide; EDCI, 1-(3-dimethylaminopropyl)-3-ethylcarbodiimide hydrochloride; Boc, tertiary-butyloxy-carbonyl; SiO2, silica gel; ES-MS, electrospray mass spectrum; TFA, trifluoroacetic acid. All solution concentrations are expressed as % volume/ % volume unless otherwise stated. Reagents were obtained from a variety of commercial sources.

IR means an infrared spectrum was obtained. $^1$H NMR means a proton magnetic resonance spectrum was obtained.

In general in this specification, "D-" or "R-" in the name of a product indicates the product is made beginning with a chiral starting material, for example (R)-phenylglycinol or (R)-valinol; however, racemization may have occurred, and the enantiomeric purity may not have been determined. For clarity and consistency, in certain cases in which $R^3$ is an alkyl group, the compounds have been named with the alkyl group considered a substituent, rather than as part of a chain including the carbon to which it is attached.

HPLC Analysis: Exterra (trademark) C18 (4.6×250 mm) column. The elution system is or consisted of a linear gradient from 90:10 (0.1% TFA in H$_2$O):(0.1% TFA in acetonitrile) to 10:90 (0.1% TFA in H$_2$O):(0.1% TFA in acetonitrile) over 40 min at 30° C. and a flow rate of 1 mL/min. UV Detection is performed from 220 to 400 nm using a photodiode array detector unless otherwise noted.

GENERAL EXPERIMENTAL PROCEDURES

The intermediate compounds and Examples may be or were prepared according to the following general procedures, with exceptions as noted, or as otherwise described below, or according to analogous procedures or other procedures known to one of ordinary skill in the art.

Coupling Method A:

The coupling of an amine and carboxylic acid to form an amide. A solution of the amine (1 equiv) and carboxylic acid (1.1 equiv) in a suitable solvent (DMF and/or methylene chloride) is treated with a carbodiimide-based dehydrating agent (e.g. DCC, or EDCI)(1.0 equiv). In general, addition of a benzotriazole-based reagent (e.g., HOBT, HBTU, or HOAT)(1 equiv) improves or improved reaction yields. After completion of the reaction as indicated by thin-layer chromatography, the mixture is partitioned between water and a suitable solvent (EtOAc and/or methylene chloride or 3:1 chloroform:isopropanol) and washed with 1 N NaOH, water, brine, and concentrated. The crude mixture is then purified, as indicated, or used directly in subsequent transformations.

Coupling Method B:

The coupling of an amine and acid chloride or acid anhydride to form an amide. A solution of the amine (1 equiv) in an appropiate solvent (chloroform, and/or methylene chloride) and pyridine (1-10 equiv) is treated with an acid chloride (1.1 equiv). After completion of the reaction as indicated by thin-layer chromatography, the mixture is partitioned between a suitable solvent (EtOAc, methylene chloride, and/or chloroform) and washed with 1 N NaOH, water, brine, and concentrated. The crude mixture is then purified, as indicated, or used directly in subsequent transformations.

Deprotection Method A:

A mixture of 10% palladium on carbon and the starting material in an appropriate solvent (EtOAc, EtOH, and/or HOAc) is placed under an atmosphere of hydrogen. Upon completion, the mixture is filtered and the filtrate concentrated. The crude mixture is then purified, as indicated, or used directly in subsequent transformations.

Deprotection Method B:

A solution of the starting material in an appropriate solvent (methylene chloride and/or chloroform) is treated with anisole (5-100 equiv) followed by trifluoroacetic acid (2-100 equiv). After completion of the reaction as indicated by thin-layer chromatography, the mixture is concentrated. The material either is partitioned between water and a suitable solvent (EtOAc, methylene chloride, and/or chloroform) and washed with 1 N NaOH, water, brine, and concentrated, or is loaded onto an ion-exchange resin (SCX, Varian) and eluted with methanol followed by 2 N ammonia in methanol. Concentration of the later fractions affords or afforded the free base product. The crude mixture is then purified, as indicated, or used directly in subsequent transformations.

Deprotection Method C:

A solution of the starting material in HOAc and HBr is heated at 70° C. After 6-15 h, the mixture is cooled, concentrated, treated with either 5 N NaOH or sodium carbonate until about pH 12, and the mixture is partitioned between EtOAc and water. The aqueous layer is washed with EtOAc (2-3×), the organic layers are or were combined and washed with water, brine, and concentrated. The crude mixture is then purified, as indicated, or used directly in subsequent transformations.

Deprotection Method D:

A solution of the starting material in an appropriate solvent (methylene chloride and/or chloroform) is treated with 4 N HCl in dioxane (2-100 equiv). After completion of the reaction as indicated by thin-layer chromatography, the mixture is concentrated to provide a hydrochloride salt. To obtain the free base, the material either is partitioned between water and a suitable solvent (EtOAc, methylene chloride, and/or chloroform) and washed with 1 N NaOH, water, brine, and concentrated, or is loaded onto an ion-exchange resin (SCX, Varian) and eluted with methanol followed by 2 N ammonia in methanol. Concentration of the later fractions affords or afforded the free base product. The crude mixture is then purified, as indicated, or used directly in subsequent transformations.

Alkylation Method A:

A solution of the starting material (1 equiv) in 5-10% HOAc in methanol (anhydrous) is treated with the indicated aldehyde or ketone (2-10 equiv) followed by sodium cyanoborohydride (2-10 equiv). After completion, the mixture is concentrated and the residue either is partitioned between a suitable solvent (EtOAc, methylene chloride, and/or chloroform) and washed with 1 N NaOH, water, brine, and concentrated, or is directly loaded onto an ion-exchange resin (SCX, Varian) and eluted with methanol followed by 2 N ammonia in methanol. Concentration of the later fractions affords or afforded the free base product. The crude mixture is then purified, as indicated, or used directly in subsequent transformations.

Alkylation Method B:

A solution of the starting material (1 equiv) in methylene chloride is treated with the indicated aldehyde or ketone (2-10 equiv) followed by sodium triacetoxyborohydride (2-10 equiv). After completion, the mixture is concentrated and the residue is partitioned between a suitable solvent (EtOAc, methylene chloride, and/or chloroform) and washed with 1 N NaOH, water, brine, and concentrated. The material is dissolved in 5% HOAc in methanol and loaded onto an ion-exchange resin (SCX, Varian) and eluted with methanol followed by 2 N ammonia in methanol. Concentration of the later fractions affords or afforded the free base product. The crude mixture is then purified, as indicated, or used directly in subsequent transformations.

Amino Alcohol Alkylation Method A:

To a 0.1 M solution of the starting amino alcohol in 5:1 to 10:1 THF:acetonitrile is added 1.2 equivalents of sodium hydride (60% dispersion in oil). The reaction flask is heated at 80° C. for 1-2 h and is then allowed to cool to room temperature. One equivalent of 4-(methane-sulfonyloxymethyl)piperidine-1-carboxylic acid tert-butyl ester is then added and the reaction is then heated at reflux temperature overnight. The reaction mixture is allowed to cool to room temperature and a saturated solution of $NaHCO_3$ is added. The layer is extracted 2-3 times with a suitable solvent (3:1 chloroform:isopropanol or EtOAc), the organic layers are or were combined, dried over $Na_2SO_4$, filtered, and concentrated to afford a crude residue. The crude residue is then purified as indicated.

HCl Salt Formation Method A:

A compound containing a basic amine is suspended in water and is treated with one equivalent of aqueous HCl. The suspension is agitated or subjected to sonication until all material is dissolved in the aqueous medium. The aqueous material is lyophilized to afford the compound as the hydrochloride salt.

HCl Salt Formation Method B:

A compound containing a basic amine is dissolved in a 4 N HCl/dioxane solution at 0° C. The solution is concentrated under reduced pressure to afford the compound as the hydrochloride salt.

PREPARATION 1

4-[(R)-2-Amino-2-phenylethoxymethyl]piperidine-1-carboxylic acid tert-butyl ester Using amino alcohol alkylation method A, (R)-phenylglycinol (4.0 g, 29 mmol) afforded, after purification (SiO2: 1:1 EtOAc:Hexane to 9:1 EtOAc:Hexane), 5.0 g (52%) of the title compound.

$^1$H NMR ES-MS m/e 335 (m+1)

PREPARATION 2

4-[2-Amino-2-(2-chlorophenyl)ethoxymethyl]piperidine-1-carboxylic acid tert-butyl ester Using amino alcohol alkylation method A, (2-chloro-phenyl)glycinol (6.6 g, 39 mmol) afforded, after purification (SiO2: 100% EtOAc), 7.5 g (53%) of the title compound.

$^1$H. NMR ES-MS m/e 369 (m+1)

PREPARATION 3

4-[2-Amino-2-(2-fluorophenyl)ethoxymethyl]piperidine-1-carboxylic acid tert-butyl ester Using amino alcohol alkylation method A, (2-fluoro-phenyl)glycinol (1.7 g, 11 mmol) afforded, after purification (SiO2: 2.5% isopropyl amine in 1:1 EtOAc:hexane), 1.7 g (43%) of the title compound.

$^1$H NMR ES-MS m/e 353 (m+1)

PREPARATION 4

4-[2-Amino-2-(4-fluorophenyl)ethoxymethyl]piperidine-1-carboxylic acid tert-butyl ester Using amino alcohol alkylation method A, (4-fluoro-phenyl)glycinol (2.5 g, 16 mmol) afforded, after purification (SiO2: 2.5% isopropyl amine in 1:1 EtOAc:hexane), 2.8 g (50%) of the title compound.

$^1$H NMR ES-MS m/e 353 (m+1)

PREPARATION 5

4-[2-Amino-2-(2-pyridinyl)ethoxymethyl]piperidine-1-carboxylic acid tert-butyl ester Using amino alcohol alkylation method A, but adding 1.1 equivalents of 4-(methanesulfonyloxymethyl)piperidine-1-carboxylic acid tert-butyl ester instead of 1 equivalent, (2-pyridinyl)glycinol (1.7 g, 12 mmol) afforded, after purification (SiO2: 0 to 5% 1 N ammonia/methanol solution in DCM), 750 mg (18%) of the title compound.

$^1$H NMR ES-MS m/e 336 (m+1)

PREPARATION 6

4-[2-Amino-2-(4-pyridinyl)ethoxymethyl]piperidine-1-carboxylic acid tert-butyl ester Using amino alcohol alkylation method A, but adding 1.1 equivalents of 4-methanesulfonyloxymethyl-piperidine-1-carboxylic acid tert-butyl ester instead of 1 equivalent, (4-pyridinyl)glycinol (440 mg, 0.44 mmol) afforded, after purification (SiO2: 0 to 5% 2 N ammonia/methanol solution in DCM), 236 mg (22%) of the title compound.

$^1$H NMR ES-MS m/e 336 (m+1)

PREPARATION 7

4-[(2R)-2-Amino-2-(isopropyl)ethoxymethyl]piperidine-1-carboxylic acid tert-butyl ester Using amino alcohol alkylation method A, (R)-valinol (0.84 g, 8.1 mmol) afforded, after purification (SiO2: 7:3:1 hexane:EtOAc:isopropyl amine), 1.4 g (55%) of the title compound.

$^1$H NMR ES-MS m/e 301 (m+1)

PREPARATION 8

4-[2-Amino-2-cyclopentylethoxymethyl]piperidine-1-carboxylic acid tert-butyl ester Using amino alcohol alkylation method A, but adding 1.1 equivalents of 4-methanesulfonyloxymethyl-piperidine-1-carboxylic acid tert-butyl ester instead of 1 equivalent, cyclopentylglycinol (1.1 g, 8.1 mmol) afforded, after purification (SiO2: 7:3:1 hexane:EtOAc:isopropyl amine), 460 mg (16%) of the title compound.

$^1$H NMR ES-MS m/e 327 (m+1)

PREPARATION 9

4-[(R)-2-Amino-2-(butyl)ethoxymethyl]piperidine-1-carboxylic acid tert-butyl ester Using amino alcohol alkylation method A, but adding 1.1 equivalents of 4-methanesulfonyloxymethyl-piperidine-1-carboxylic acid tert-butyl ester instead of 1 equivalent, (R)-norleucinol (400 mg, 3.4 mmol) afforded, after purification (SiO2: 7:3:1 hexane:EtOAc:isopropyl amine), 195 mg (18%) of the title compound.

$^1$H NMR ES-MS m/e 313 (m−1)

PREPARATION 10

4-{(R)-2-[(3-Chloro-1H-indole-6-carbonyl)amino]-2-phenyl-ethoxymethyl}piperidine-1-carboxylic acid tert-butyl ester Using coupling method A, 4-[(R)-2-amino-2-phenylethoxy-methyl]piperidine-1-carboxylic acid tert-butyl ester (3 g, 9.0 mmol) and 3-chloroindole-6-carboxylic acid (1.7 g, 9.0 mmol) afforded the title compound as a crude residue, which was used without further purification.

$^1$H NMR ES-MS m/e 510 (m−1)

PREPARATION 11

4-{(R)-2-[(3-Methyl-1H-indole-6-carbonyl)amino]-2-phenyl-ethoxymethyl}piperidine-1-carboxylic acid tert-butyl ester Using coupling method A, 4-[(R)-2-amino-2-phenylethoxy-methyl)piperidine-1-carboxylic acid tert-butyl ester (1 g, 3.0 mmol) and 3-methylindole-6-carboxylic acid (0.54 g, 3.0 mmol) afforded the title compound as a crude residue, which was used without further purification.

$^1$H NMR ES-MS m/e 492 (m+1)

PREPARATION 12

4-{2-[(3-Chloro-1H-indole-6-carbonyl)amino]-2-(2-chloro-phenyl)ethoxymethyl}piperidine-1-carboxylic acid tert-butyl ester Using coupling method A, 4-[2-amino-2-(2-chlorophenyl)-ethoxymethyl]piperidine-1-carboxylic acid tert-butyl ester (7.5 g, 20 mmol) and 3-chloroindole-6-carboxylic acid (3.9 g, 20 mmol) afforded, after purification (SiO2: 33% to 50% EtOAc in hexane), 8 g (73%) of the title compound.

$^1$H NMR ES-MS m/e 546 (m+1)

PREPARATION 13

4-{2-(1H-Indole-6-carbonyl)amino-2-(2-chlorophenyl)ethoxy-methyl}piperidine-1-carboxylic acid tert-butyl ester Using coupling method A, 4-[2-amino-2-(2-chlorophenyl)-ethoxymethyl]piperidine-1-carboxylic acid tert-butyl ester (500 mg, 1.4 mmol) and indole-6-carboxylic acid (219 mg, 1.4 mmol) afforded, after purification (SiO2: 33% to 50% EtOAc in hexane), 579 mg (83%) of the title compound.

$^1$H NMR ES-MS m/e 512 (m+1)

PREPARATION 14

4-{2-(5-Chloro-1H-indole-2-carbonyl)amino-2-(2-chloro-phenyl)ethoxymethyl}piperidine-1-carboxylic acid tert-butyl ester Using coupling method A, 4-[2-amino-2-(2-chlorophenyl)-ethoxymethyl]piperidine-1-carboxylic acid tert-butyl ester (300 mg, 0.8 mmol) and 5-chloroindole-2-carboxylic acid (158 mg, 1.4 mmol) afforded, after purification (SiO2: 33% EtOAc in hexane), 407 mg (92%) of the title compound.

$^1$H NMR ES-MS m/e 546 (m+1)

PREPARATION 15

4-{2-[(6-Chlorobenzo[b]thiophene-2-carbonyl)amino]-2-(2-chlorophenyl)ethoxymethyl}piperidine-1-carboxylic acid tert-butyl ester Using coupling method A, 4-[2-amino-2-(2-chlorophenyl)-ethoxymethyl]piperidine-1-carboxylic acid tert-butyl ester (300 mg, 0.8 mmol) and 6-chlorobenzo[b]thiophene-2-carboxylic acid (172 mg, 0.8 mmol) afforded, after purification (SiO2: 50% EtOAc in hexane), 353 mg (77%) of the title compound.

$^1$H NMR ES-MS m/e 563 (m+1)

PREPARATION 16

4-{2-[(3-Chloro-1H-indole-6-carbonyl)amino]-2-(2-fluoro-phenyl)ethoxymethyl}piperidine-1-carboxylic acid tert-butyl ester Using coupling method A, 4-[2-amino-2-(2-fluorophenyl)-ethoxymethyl]piperidine-1-carboxylic acid tert-butyl ester (600 mg, 1.7 mmol) and 3-chloroindole-6-carboxylic acid (367 mg, 1.9 mmol) afforded, after purification (SiO2: 10 DCM: 2 EtOAc: 2 Hexane: 0 to 0.125 isopropyl amine), 800 mg (90%) of the title compound.

$^1$H NMR ES-MS m/e 531 (m+1)

PREPARATION 17

4-{2-[(1H-Indole-6-carbonyl)amino]-2-(2-fluorophenyl)ethoxy-methyl}piperidine-1-carboxylic acid tert-butyl ester Using coupling method A, 4-[2-amino-2-(2-fluorophenyl)-ethoxymethyl]piperidine-1-carboxylic acid tert-butyl ester (480 mg, 1.4 mmol) and indole-6-carboxylic acid (242 mg, 1.5 mmol) afforded, after purification (SiO2: 0 to 40% 2 N ammonia/methanol solution in DCM), 355 mg (53%) of the title compound.

$^1$H NMR ES-MS m/e 496 (m+1)

PREPARATION 18

4-{2-[(3-Chloro-1H-indole-6-carbonyl)amino]-2-(4-fluoro-phenyl)ethoxymethyl}piperidine-1-carboxylic acid tert-butyl ester Using coupling method A, 4-[2-amino-2-(4-fluorophenyl)-ethoxymethyl]piperidine-1-carboxylic acid tert-butyl ester (1.1 g, 3.0 mmol) and 3-chloroindole-6-carboxylic acid (653 mg, 3.3 mmol) afforded 1.6 g (100%) of the title compound as a crude residue, which was used without further purification.

$^1$H NMR ES-MS m/e 531 (m+1)

PREPARATION 19

4-{2-[(1H-Indole-6-carbonyl)amino]-2-(4-fluorophenyl)ethoxy-methyl}piperidine-1-carboxylic acid tert-butyl ester Using coupling method A, 4-[2-amino-2-(4-fluorophenyl)-ethoxymethyl]piperidine-1-carboxylic acid tert-butyl ester (1.0 g, 2.9 mmol) and 3-indole-6-carboxylic acid (513 mg, 3.2 mmol) afforded 1.4 g (100%) of the title compound as a crude residue, which was used without further purification.

$^1$H NMR ES-MS m/e 531 (m+1)

PREPARATION 20

4-{2-[(3-Chloro-1H-indole-6-carbonyl)amino]-2-(2-pyridinyl)-ethoxymethyl}piperidine-1-carboxylic acid tert-butyl ester Using coupling method A, 4-[2-amino-2-(2-pyridinyl)-ethoxymethyl]piperidine-1-carboxylic acid tert-butyl ester (730 mg, 2.2 mmol) and 3-chloroindole-6-carboxylic acid (468 mg, 2.4 mmol) afforded, after purification (SiO2: 10 DCM:2 EtOAc:2 Hexane:0 to 1.5 isopropyl amine), 835 mg (64%) of the title compound.

$^1$H NMR ES-MS m/e 514 (m+1)

PREPARATION 21

4-{2-[(3-Chloro-1H-indole-6-carbonyl)amino]-2-(4-pyridinyl)-ethoxymethyl}piperidine-1-carboxylic acid tert-butyl ester Using coupling method A, 4-[2-amino-2-(4-pyridinyl)-ethoxymethyl]piperidine-1-carboxylic acid tert-butyl ester (233 mg, 0.69 mmol) and 3-chloroindole-6-carboxylic acid (149 mg, 0.76 mmol) afforded, after purification (SiO2: 10 DCM:2 EtOAc:2 Hexane:3 isopropyl amine), 118 mg (33%) of the title compound.
$^1$H NMR ES-MS m/e 514 (m+1)

PREPARATION 22

4-{2-[(3-Chloro-1H-indole-6-carbonyl)amino]-2-cyclopentyl-ethoxymethyl}piperidine-1-carboxylic acid tert-butyl ester Using coupling method A, 4-(2-amino-2-cyclopentyl-ethoxymethyl)piperidine-1-carboxylic acid tert-butyl ester (460 mg, 1.4 mmol) and 3-chloroindole-6-carboxylic acid (275 mg, 1.4 mmol) afforded, after purification (SiO2: 40% EtOAc in hexane), 211 mg (30%) of the title compound.
$^1$H NMR ES-MS m/e 504 (m+1)

PREPARATION 23

4-{(R)-2-[(3-Chloro-1H-indole-6-carbonyl)amino]-2-(butyl)-ethoxymethyl}piperidine-1-carboxylic acid tert-butyl ester Using coupling method A, 4-[(R)-2-amino-2-(butyl)-ethoxymethyl]piperidine-1-carboxylic acid tert-butyl ester (195 mg, 0.62 mmol) and 3-chloroindole-6-carboxylic acid (133 mg, 0.68 mmol) afforded, after purification (SiO2: 40% EtOAc in hexane), 90 mg (29%) of the title compound.
$^1$H NMR ES-MS m/e 504 (m+1)

PREPARATION 24

4-[(R)-2-Benzyloxycarbonylamino-2-phenylethoxymethyl)-piperidine-1-carboxylic acid tert-butyl ester Using coupling method B, 4-[(R)-2-amino-2-phenylethoxy-methyl)piperidine-1-carboxylic acid tert-butyl ester (2 g, 6.0 mmol) and dibenzyl dicarbonate (2.1 g, 7.2 mmol) afforded 3.4 g (100%) of the title compound as a crude residue, which was used without further purification.
$^1$H NMR ES-MS m/e 469 (m+1)

PREPARATION 25

4-[(2R)-2-Benzyloxycarbonylamino-2-(isopropyl)ethoxymethyl]-piperidine-1-carboxylic acid tert-butyl ester Using coupling method B, 4-[(2R)-2-amino-2-(isopropyl)-ethoxymethyl]piperidine-1-carboxylic acid tert-butyl ester (1.3 g, 4.5 mmol) and dibenzyl dicarbonate (1.5 g, 5.3 mmol) afforded 1.9 g (100%) of the title compound as a crude residue, which was used without further purification.
$^1$H NMR ES-MS m/e 435 (m+1)

EXAMPLE 1

3-Chloro-N-[(R)-1-phenyl-2-(piperidin-4-yl-methoxy)ethyl]-1H-indole-6-carboxamide hydrochloride Using deprotection method D, 4-{(R)-2-[(3-chloro-1H-indole-6-carbonyl)amino]-2-phenylethoxymethyl}piperidine-1-carboxylic acid tert-butyl ester (1.7 g crude, 3.2 mmol) afforded 1.4 g (97%) of the title compound as a crude residue, which was used without further purification.
$^1$H NMR ES-MS m/e 412 (m+1)

PREPARATION OF THE FREE BASE

3-Chloro-N-[(R)-1-phenyl-2-(piperidin-4-yl-methoxy)ethyl]-1H-indole-6-carboxamide Using deprotection method B, but without addition of anisole, 4-{(R)-2-[(3-chloro-1H-indole-6-carbonyl)amino]-2-phenylethoxymethyl}piperidine-1-carboxylic acid tert-butyl ester (4.6 g crude, 8.97 mmol) afforded 5 g (100%) of the title compound as a crude residue, which was used without further purification.
$^1$H NMR ES-MS m/e 412 (m+1)

PREPARATION 26

3-Methyl-N-[(R)-1-phenyl-2-(piperidin-4-yl-methoxy)ethyl]-1H-indole-6-carboxamide Using deprotection method B, but without addition of anisole, 4-{(R)-2-[(3-methyl-1H-indole-6-carbonyl)amino]-2phenylethoxymethyl}piperidine-1-carboxylic acid tert-butyl ester (1.5 g crude, 3.0 mmol) afforded the title compound as a crude residue, which was used without further purification.
$^1$H NMR ES-MS m/e 392 (m+1)

PREPARATION 27

3-Chloro-N-[1-(2-chlorophenyl)-2-(piperidin-4-yl-methoxy)-ethyl]-1H-indole-6-carboxamide Using deprotection method D, 4-{2-[(3-chloro-1H-indole-6-carbonyl)amino]-2-(2-chlorophenyl)ethoxymethyl}piperidine-1-carboxylic acid tert-butyl ester (8 g, 14 mmol) afforded 6.1 g (94%) of the title compound as a crude residue, which was used without further purification.
$^1$H NMR ES-MS m/e 446 (m+1)

PREPARATION 28

N-[1-(2-Chlorophenyl)-2-(piperidin-4-ylmethoxy)ethyl]-1H-indole-6-carboxamide

Using deprotection method D, 4-{2-(1H-indole-6-carbonyl)amino-2-(2-chlorophenyl)ethoxymethyl}piperidine-1-carboxylic acid tert-butyl ester (270 mg, 0.53 mmol) afforded 200 mg (92%) of the title compound as a crude residue, which was used without further purification.
$^1$H NMR ES-MS m/e 412 (m+1)

PREPARATION 29

5-Chloro-N-[1-(2-chlorophenyl)-2-(piperidin-4-yl-methoxy)-ethyl]-1H-indole-2-carboxamide Using deprotection method D, 4-{2-(5-chloro-1H-indole-2-carbonyl)amino-2-(2-chlorophenyl)ethoxymethyl}piperidine-1-carboxylic acid tert-butyl ester (400 mg, 0.73 mmol) afforded, after SCX purification, 326 mg (95%) of the title compound.

$^1$H NMR ES-MS m/e 446 (m+1)

PREPARATION 30

6-Chloro-N-[1-(2-chlorophenyl)-2-(piperidin-4-yl-methoxy)-ethyl]benzo[b]thiophene-2-carboxamide Using deprotection method D, 4-{2-[(6-chlorobenzo[b]-thiophene-2-carbonyl)amino]-2-(2-chlorophenyl)ethoxymethyl}-piperidine-1-carboxylic acid tert-butyl ester (345 mg, 0.61 mmol) afforded, after SCX purification, 260 mg (92%) of the title compound.

$^1$H NMR ES-MS m/e 463 (m+1)

PREPARATION 31

3-Chloro-N-[1-(2-fluorophenyl)-2-(piperidin-4-yl-methoxy)-ethyl]-1H-indole-6-carboxamide Using deprotection method D, 4-{2-[(3-chloro-1H-indole-6-carbonyl)amino]-2-(2-fluorophenyl)ethoxymethyl}piperidine-1-carboxylic acid tert-butyl ester (750 mg, 1.4 mmol) afforded, after SCX purification, 553 mg (91%) of the title compound.

$^1$H NMR ES-MS m/e 430 (m+1)

PREPARATION 32

N-[1-(2-Fluorophenyl)-2-(piperidin-4-ylmethoxy)ethyl]-1H-indole-6-carboxamide Using deprotection method D, 4-{2-[(1H-indole-6-carbonyl)amino]-2-(2-fluorophenyl)ethoxymethyl}piperidine-1-carboxylic acid tert-butyl ester (350 mg, 0.71 mmol) afforded, after SCX purification, 135 mg (48%) of the title compound.

$^1$H NMR ES-MS m/e 396 (m+1)

PREPARATION 33

3-Chloro-N-[1-(4-fluorophenyl)-2-(piperidin-4-yl-methoxy)-ethyl]-1H-indole-6-carboxamide Using deprotection method B, but without addition of anisole, 4-{2-[(3-chloro-1H-indole-6-carbonyl)amino]-2-(4-fluorophenyl)ethoxymethyl}piperidine-1-carboxylic acid tert-butyl ester (2.3 g, 4.3 mmol) afforded, after purification (SiO2: 25% isopropyl amine in ethyl acetate), 1.0 g (54%) of the title compound.

$^1$H NMR ES-MS m/e 430 (m+1)

PREPARATION 34

N-[1-(4-Fluorophenyl)-2-(piperidin-4-ylmethoxy)ethyl]-1H-indole-6-carboxamide Using deprotection method B, but without addition of anisole, 4-{2-[(1H-indole-6-carbonyl)amino]-2-(4-fluoro-phenyl)ethoxymethyl}piperidine-1-carboxylic acid tert-butyl ester (1.6 g, 3.2 mmol) afforded 1.3 g (100%) of the title compound as a crude residue which was used without further purification.

$^1$H NMR ES-MS m/e 430 (m+1)

PREPARATION 35

3-Chloro-N-[1-(2-pyridinyl)-2-(piperidin-4-yl-methoxy)ethyl]-1H-indole-6-carboxamide Using deprotection method D, 4-{2-[(3-chloro-1H-indole-6-carbonyl)amino]-2-(2-pyridinyl)ethoxymethyl}piperidine-1-carboxylic acid tert-butyl ester (200 mg, 0.39 mmol) afforded 160 g (100%) of the title compound as a crude residue, which was used without further purification.

$^1$H NMR ES-MS m/e 413 (m+1)

PREPARATION 36

3-Chloro-N-[1-(4-pyridinyl)-2-(piperidin-4-yl-methoxy)ethyl]-1H-indole-6-carboxamide Using deprotection method B, but without addition of anisole, 4-{2-[(3-chloro-1H-indole-6-carbonyl)amino]-2-(4-pyridinyl)ethoxymethyl}piperidine-1-carboxylic acid tert-butyl ester (83 mg, 0.16 mmol) afforded 67 mg (100%) of the title compound as a crude residue, which was used without further purification.

$^1$H NMR ES-MS m/e 413 (m+1)

PREPARATION 37

3-Chloro-N-[1-cyclopentyl-2-(piperidin-4-yl-methoxy)ethyl]-1H-indole-6-carboxamide Using deprotection method D, 4-{2-[(3-chloro-1H-indole-6-carbonyl)amino]-2-cyclopentylethoxymethyl}piperidine-1-carboxylic acid tert-butyl ester (211 mg, 0.42 mmol) afforded, after SCX purification, 140 mg (83%) of the title compound.

$^1$H NMR ES-MS m/e 402 (m−1)

PREPARATION 38

3-Chloro-N-[1-butyl-2-(piperidin-4-ylmethoxy)ethyl]-1H-indole-6-carboxamide

Using deprotection method D, 4-{(R)-2-[(3-chloro-1H-indole-6-carbonyl)amino]-2-butylethoxymethyl}piperidine-1-carboxylic acid tert-butyl ester (90 mg, 0.18 mmol) afforded, after SCX purification, the title compound a's a crude residue, which was used without further purification. ES-MS m/e 397 (m+1)

PREPARATION 39

Benzyl N-[(R)-1-Phenyl-2-(piperidin-4-ylmethoxy)ethyl]-carbamate hydrochloride

Using deprotection method D, 4-[(R)-2-benzyloxy-carbonylamino-2-phenylethoxymethyl)piperidine-1-carboxylic acid tert-butyl ester (3.7 g, 7.9 mmol) afforded 3.7 g (100%) of the title compound as a crude residue, which was used without further purification.

$^1$H NMR ES-MS m/e 369 (m+1)

PREPARATION 40

Benzyl N-[(R)-1-(Isopropyl)-2-(piperidin-4-yl-methoxy)ethyl]-carbamate

Using deprotection method D, crude 4-[(2R)-2-benzyloxy-carbonylamino-2-(isopropyl)ethoxymethyl]piperidine-1-carboxylic acid tert-butyl ester (4.5 mmol) afforded, after SCX purification and then further purification (SiO2: 60 to 100% EtOAc in DCM), 1.1 g (72%) of the title compound.

$^1$H NMR ES-MS m/e 335 (m+1)

EXAMPLE 2

3-Chloro-N-[(R)-1-phenyl-2-(1-isopropylpiperidin-4-yl-methoxy)ethyl]-1H-indole-6-carboxamide Using alkylation method A, 3-chloro-N-[(R)-1-phenyl-2-(piperidin-4-ylmethoxy)ethyl]-1H-indole-6-carboxamide (8.97 mmol) and acetone (6.6 mL, 90 mmol) afforded, after purification (SiO2: 8:2:1 hexane:EtOAc:isopropylamine), 2.2 g (54%) of the title compound.

$^1$H NMR ES-MS m/e 454 (m+1)

EXAMPLE 2a

3-Chloro-N-[(R)-1-phenyl-2-(1-isopropylpiperidin-4-yl-methoxy)ethyl]-1H-indole-6-carboxamide hydrochloride Using alkylation method A, 3-chloro-N-[(R)-1-phenyl-2-(piperidin-4-ylmethoxy)ethyl]-1H-indole-6-carboxamide (200 mg, 0.45 mmol) and acetone (0.33 mL, 4.5 mmol) afforded, after purification (SiO2: 8:2:1 hexane:EtOAc:isopropylamine) and conversion to the HCl salt by general method B, 120 mg (55%) of the title compound.

$^1$H NMR ES-MS m/e 454 (m+1)

EXAMPLE 3

3-Chloro-N-[(R)-1-phenyl-2-(1-cyclopentylpiperidin-4-yl-methoxy)ethyl]-1H-indole-6-carboxamide Using alkylation method A, 3-chloro-N-[(R)-1-phenyl-2-(piperidin-4-ylmethoxy)ethyl]-1H-indole-6-carboxamide hydrochloride (150 mg, 0.33 mmol) and cyclopentanone (0.5 mL, 5.7 mmol) afforded, after purification (SiO2: 8:2:1 hexane:EtOAc:isopropylamine), 78 mg (49%) of the title compound.

$^1$H NMR ES-MS m/e 481 (m+1)

EXAMPLE 4

3-Chloro-N-[(R)-1-phenyl-2-(1-methylpiperidin-4-yl-methoxy)ethyl]-1H-indole-6-carboxamide Using alkylation method B, 3-chloro-N-[(R)-1-phenyl-2-(piperidin-4-ylmethoxy)ethyl]-1H-indole-6-carboxamide hydrochloride (200 mg, 0.44 mmol) and paraformaldehyde (134 mg, 4.4 mmol) afforded, after purification (SiO2: 2.5% isopropylamine in 10:2:2:DCM:EtOAc:hexane), 80 mg (42%) of the title compound.

$^1$H NMR ES-MS m/e 426 (m+1)

EXAMPLE 5

3-Chloro-N-[(R)-1-phenyl-2-(1-cyclopropylpiperidin-4-yl-methoxy)ethyl]-1H-indole-6-carboxamide hydrochloride Using alkylation method A with addition of 3A molecular sieves, 3-chloro-N-[(R)-1-phenyl-2-(piperidin-4-yl-methoxy)-ethyl]-1H-indole-6-carboxamide hydrochloride (200 mg, 0.44 mmol) and [(1-ethoxycyclopropyl)oxy]trimethylsilane (0.53 mL, 2.7 mmol) afforded, after purification (SiO2: 0 to 5% isopropylamine in 10:2:2:DCM:EtOAc:hexane) and after conversion to the HCl salt by general method B, 80 mg (40%) of the title compound.

$^1$H NMR ES-MS m/e 452 (m+1)

EXAMPLE 6

3-Chloro-N-[(R)-1-phenyl-2-[1-(4-pyridinyl)piperidin-4-yl-methoxy]ethyl]-1H-indole-6-carboxamide To a suspension of 3-chloro-N-[(R)-1-phenyl-2-(piperidin-4-ylmethoxy)ethyl]-1H-indole-6-carboxamide (1.0 g, 2.2 mmol) in 20 mL of EtOH was added triethylamine (1.56 mL, 11 mmol) and 4-chloropyridine hydrochloride (336 mg, 2.2 mmol). Heating the mixture at 120° C. in a sealed tube afforded, after purification (SiO2: 8:2:1 hexane:EtOAc:isopropylamine), 185 mg (16%) of the title compound.

$^1$H NMR ES-MS m/e 523 (m+1)

EXAMPLE 7

3-Methyl-N-[(R)-1-phenyl-2-(1-isopropylpiperidin-4-yl-methoxy)ethyl]-1H-indole-6-carboxamide Using alkylation method A, 3-methyl-N-[(R)-1-phenyl-2-(piperidin-4-ylmethoxy)ethyl]-1H-indole-6-carboxamide (400 mg, 1.0 mmol) and acetone (0.75 mL, 10 mmol) afforded, after purification (SiO2: 8:2:1 hexane:EtOAc:isopropylamine), 197 mg (44%) of the title compound.

$^1$H NMR ES-MS m/e 434 (m+1)

EXAMPLE 8

3-Chloro-N-[1-(2-chlorophenyl)-2-(1-isopropylpiperidin-4-yl-methoxy)ethyl]-1H-indole-6-carboxamide hydrochloride Using deprotection method B, 3-chloro-N-[1-(2-chlorophenyl)-2-(1-isopropylpiperidin-4-ylmethoxy)ethyl]-1H-indole-6-carboxamide (128 mg, 0.26 mmol) afforded 122 mg (88%) of the title compound.

$^1$H NMR ES-MS m/e 488 (m+1)

EXAMPLE 8a

3-Chloro-N-[1-(2-chlorophenyl)-2-(1-isopropylpiperidin-4-yl-methoxy)ethyl]-1H-indole-6-carboxamide Using alkylation method A, 3-chloro-N-[1-(2-chloro-phenyl)-2-(piperidin-4-ylmethoxy)ethyl]-1H-indole-6-carboxamide (200 mg, 0.41 mmol) and acetone (2.5 mL, 54 mmol) afforded, after purification (SiO2: 10:10:1 hexane:EtOAc:isopropylamine), 132 mg (66%) of the title compound.
$^1$H NMR ES-MS m/e 488 (m+1)

EXAMPLE 9

3-Chloro-N-[1-(2-chlorophenyl)-2-(1-methylpiperidin-4-yl-methoxy)ethyl]-1H-indole-6-carboxamide Using alkylation method B, 3-chloro-N-[1-(2-chloro-phenyl)-2-(piperidin-4-ylmethoxy)ethyl]-1H-indole-6-carboxamide (300 mg, 0.67 mmol) and paraformaldehyde (201 mg, 6.7 mmol) afforded, after purification (SiO2: 10:10:1 hexane:EtOAc:isopropylamine), 175 mg (57%) of the title compound.
$^1$H NMR ES-MS m/e 461 (m+1)

EXAMPLE 10

3-Chloro-N-[1-(2-chlorophenyl)-2-(1-ethylpiperidin-4-yl-methoxy)ethyl]-1H-indole-6-carboxamide Using alkylation method A, 3-chloro-N-[1-(2-chloro-phenyl)-2-(piperidin-4-ylmethoxy)ethyl]-1H-indole-6-carboxamide (600 mg, 1.3 mmol) and acetaldehyde (0.4 mL, 6.7 mmol) afforded, after purification (SiO2: 10:10:1 hexane:EtOAc:isopropylamine) and recrystallization (acetonitrile), 275 mg (43%) of the title compound.
$^1$H NMR ES-MS m/e 475 (m+1)

EXAMPLE 11

3-Chloro-N-[1-(2-chlorophenyl)-2-[1-(2-fluoroethyl)-piperidin-4-ylmethoxy]ethyl]-1H-indole-6-carboxamide To a solution of 3-chloro-N-[1-(2-chlorophenyl)-2-(piperidin-4-ylmethoxy)ethyl]-1H-indole-6-carboxamide (600 mg, 1.3 mmol) in 6 mL of DMSO was added potassium carbonate (716 mg, 5.2 mmol) and 2-bromo-1-fluoroethane (0.10 mL, 1.1 mmol). The reaction was allowed to stir at room temperature overnight after which time water was added and the resulting precipitate was isolated by filtration. Purification of the filtrate (SiO2: EtOAc) provided 178 mg (28%) of the title compound.
$^1$H NMR ES-MS m/e 493 (m+1)

EXAMPLE 12

3-Chloro-N-[1-(2-chlorophenyl)-2-[1-(2,2,2-trifluoroacetyl)-piperidin-4-ylmethoxy]ethyl]-1H-indole-6-carboxamide To a solution of 3-chloro-N-[1-(2-chlorophenyl)-2-(piperidin-4-ylmethoxy)ethyl]-1H-indole-6-carboxamide (600 mg, 1.3 mmol) in 5 mL of methanol was added triethylamine (0.37 mL, 2.7 mmol) and trifluoroacetic acid ethyl ester (0.20 mL, 2.7 mmol). The reaction was allowed to stir at room temperature overnight after which time water was added and the resulting precipitate was isolated by filtration. Purification of the filtrate (SiO2: 10:2:0.5 DCM:hexane:isopropylamine) provided 297 mg (41%) of the title compound.
$^1$H NMR ES-MS m/e 543 (m+1)

EXAMPLE 13

3-Chloro-N-[1-(2-chlorophenyl)-2-[1-(2,2,2-trifluoroethyl)-piperidin-4-ylmethoxy]ethyl]-1H-indole-6-carboxamide To a solution of 3-chloro-N-[1-(2-chlorophenyl)-2-(piperidin-4-ylmethoxy)ethyl]-1H-indole-6-carboxamide (700 mg, 1.6 mmol) in 5 mL of DMSO was added potassium carbonate (1.0 g, 7.9 mmol) and 2,2,2-trifluoroethyl trifluoromethanesulfonate (364 mg, 1.6 mmol). The reaction was allowed to stir at room temperature overnight after which time water was added and the resulting precipitate was isolated by filtration. Purification of the filtrate (SiO2: 30% EtOAc in hexane) provided 250 mg (30%) of the title compound.
$^1$H NMR ES-MS m/e 529 (m+1)

EXAMPLE 14

3-Chloro-N-[1-(2-chlorophenyl)-2-[1-(2-hydroxyethyl)-piperidin-4-ylmethoxy]ethyl]-1H-indole-6-carboxamide To a solution of 3-chloro-N-[1-(2-chlorophenyl)-2-(piperidin-4-ylmethoxy)ethyl]-1H-indole-6-carboxamide (200 mg, 0.45 mmol) in 5 mL of EtOH was added potassium carbonate (247 mg, 1.8 mmol), potassium iodide (224 mg, 1.4 mmol) and 2-chloroethanol (0.09 mL, 1.4 mmol). The reaction was allowed to stir at room temperature overnight after which time water was added and the resulting precipitate was isolated by filtration. Purification of the filtrate (SiO2: 10:0.5 EtOAc:isopropylamine) provided 70 mg (32%) of the title compound.
$^1$H NMR ES-MS m/e 491 (m+1)

EXAMPLE 15

5-Chloro-N-[1-(2-chlorophenyl)-2-(1-isopropylpiperidin-4-yl-methoxy)ethyl]-1H-indole-2-carboxamide Using alkylation method A, 5-chloro-N-[1-(2-chloro-phenyl)-2-(piperidin-4-ylmethoxy)ethyl]-1H-indole-2-carboxamide (320 mg, 0.72 mmol) and acetone (2.0 mL, 27 mmol) afforded, after purification (SiO2: 0 to 2.5% isopropylamine in 1:1 hexane:EtOAc) and recrystallization (acetonitrile), 185 mg (53%) of the title compound.
$^1$H NMR ES-MS m/e 488 (m+1)

EXAMPLE 16

6-Chloro-N-[1-(2-chlorophenyl)-2-(1-isopropylpiperidin-4-yl-methoxy)ethyl]benzo[b]thiophene-2-carboxamide Using alkylation method A, 6-chloro-N-[1-(2-chloro-phenyl)-2-(piperidin-4-ylmethoxy)ethyl]benzo[b]thiophene-2-carboxamide (255 mg, 0.55 mmol) and acetone (2.0 mL, 27 mmol) afforded, after purification (SiO2: 4:4:1 hexane EtOAc:isopropylamine), 150 mg (54%) of the title compound.
$^1$H NMR ES-MS m/e 505 (m+1)

EXAMPLE 17

N-[1-(2-Chlorophenyl)-2-(1-isopropylpiperidin-4-ylmethoxy)-ethyl]-1H-indole-6-carboxamide Using alkylation method A, N-[1-(2-chlorophenyl)-2-(piperidin-4-ylmethoxy)ethyl]-1H-indole-6-carboxamide (195 mg, 0.47 mmol) and acetone (2.0 mL, 27 mmol) afforded, after purification (SiO2: 0 to 2.5% isopropylamine in 1:1 hexane:EtOAc), 120 mg (60%) of the title compound.

$^1$H NMR ES-MS m/e 454 (m+1)

EXAMPLE 18

3-Chloro-N-[1-(2-fluorophenyl)-2-(1-isopropylpiperidin-4-yl-methoxy)ethyl]-1H-indole-6-carboxamide Using alkylation method A, 3-chloro-N-[1-(2-fluoro-phenyl)-2-(piperidin-4-ylmethoxy)ethyl]-1H-indole-6-carboxamide (303 mg, 0.71 mmol) and acetone (2 mL, 27 mmol) afforded 260 mg (78%) of the title compound.

$^1$H NMR ES-MS m/e 472 (m+1)

EXAMPLE 19

3-Chloro-N-[1-(2-fluorophenyl)-2-(1-methylpiperidin-4-yl-methoxy)ethyl]-1H-indole-6-carboxamide Using alkylation method B, 3-chloro-N-[1-(2-fluoro-phenyl)-2-(piperidin-4-ylmethoxy)ethyl]-1H-indole-6-carboxamide (250 mg, 0.58 mmol) and paraformaldehyde (174 mg, 5.8 mmol) afforded, after purification (SiO2: 10:2:2:1 DCM:EtOAc:hexane:isopropylamine), 160 mg (63%) of the title compound.

$^1$H NMR ES-MS m/e 445 (m+1)

EXAMPLE 20

N-[1-(2-Fluorophenyl)-2-(1-isopropylpiperidin-4-ylmethoxy)-ethyl]-1H-indole-6-carboxamide Using alkylation method A, N-[1-(2-fluorophenyl)-2-(piperidin-4-ylmethoxy)ethyl]-1H-indole-6-carboxamide (135 mg, 0.34 mmol) and acetone (1 mL, 14 mmol) afforded, after purification (SiO2: 10:2:2:1 DCM:EtOAc:hexane:isopropylamine), 90 mg (60%) of the title compound.

$^1$H NMR ES-MS m/e 438 (m+1)

EXAMPLE 21

3-Chloro-N-[1-(4-fluorophenyl)-2-(1-isopropylpiperidin-4-yl-methoxy)ethyl]-1H-indole-6-carboxamide Using alkylation method A, 3-chloro-N-[1-(4-fluoro-phenyl)-2-(piperidin-4-ylmethoxy)ethyl]-1H-indole-6-carboxamide (600 mg, 1.4 mmol) and acetone (10 mL, 135 mmol) afforded, after trituration (acetonitrile), 500 mg (76%) of the title compound.

$^1$H NMR ES-MS m/e 472 (m+1)

EXAMPLE 22

3-Chloro-N-[1-(4-fluorophenyl)-2-(1-methylpiperidin-4-yl-methoxy)ethyl]-1H-indole-6-carboxamide Using alkylation method B, 3-chloro-N-[1-(4-fluoro-phenyl)-2-(piperidin-4-ylmethoxy)ethyl]-1H-indole-6-carboxamide (373 mg, 0.87 mmol) and paraformaldehyde (520 mg, 17 mmol) afforded, after purification (SiO2: 8:2:1 hexane:EtOAc:isopropylamine), 115 mg (30%) of the title compound.

$^1$H NMR ES-MS m/e 444 (m+1)

EXAMPLE 23

N-[1-(4-Fluorophenyl)-2-(1-isopropylpiperidin-4-ylmethoxy)-ethyl]-1H-indole-6-carboxamide Using alkylation method A, N-[1-(4-fluorophenyl)-2-(piperidin-4-ylmethoxy)ethyl]-1H-indole-6-carboxamide (900 mg, 2.3 mmol) and acetone (25 mL, 340 mmol) afforded, after purification (SiO2: 8:2:1 hexane:EtOAc:isopropylamine), 45 mg (5%) of the title compound.

$^1$H NMR ES-MS m/e 438 (m+1)

EXAMPLE 24

3-Chloro-N-[1-(2-pyridinyl)-2-(1-isopropylpiperidin-4-yl-methoxy)ethyl]-1H-indole-6-carboxamide Using alkylation method A, 3-chloro-N-[1-(2-pyridinyl)-2-(piperidin-4-ylmethoxy)ethyl]-1H-indole-6-carboxamide (170 mg, 0.41 mmol) and acetone (1.2 mL, 16.8 mmol) afforded 130 mg (70%) of the title compound.

$^1$H NMR ES-MS m/e 456 (m+1)

EXAMPLE 24a

3-Chloro-N-[1-(2-pyridinyl)-2-(1-isopropylpiperidin-4-yl-methoxy)ethyl]-1H-indole-6-carboxamide hydrochloride Using deprotection method A, 3-chloro-N-[1-(2-pyridinyl)-2-(1-isopropylpiperidin-4-ylmethoxy)ethyl]-1H-indole-6-carboxamide (105 mg, 0.25 mmol) and acetone (1.2 mL, 16.8 mmol) afforded 110 mg (96%) of the title compound.

$^1$H NMR ES-MS m/e 456 (m+1)

EXAMPLE 25

3-Chloro-N-[1-(2-pyridinyl)-2-(1-methylpiperidin-4-yl-methoxy)ethyl]-1H-indole-6-carboxamide Using alkylation method B, 3-chloro-N-[1-(2-pyridinyl)-2-(piperidin-4-ylmethoxy)ethyl]-1H-indole-6-carboxamide (30 mg, 0.07 mmol) and paraformaldehyde (15 mg, 0.12 mmol) afforded, after purification (SiO2: 10% isopropylamine in DCM), 20 mg (65%) of the title compound.

$^1$H NMR ES-MS m/e 427 (m+1)

EXAMPLE 26

3-Chloro-N-[1-(4-pyridinyl)-2-(1-isopropylpiperidin-4-yl-methoxy)ethyl]-1H-indole-6-carboxamide Using alkylation method A, 3-chloro-N-[1-(4-pyridinyl)-2-(piperidin-4-ylmethoxy)ethyl]-1H-indole-6-carboxamide (67 mg, 0.16 mmol) and acetone (2 mL, 27 mmol) afforded 35 mg (47%) of the title compound.
$^1$H NMR ES-MS m/e 455 (m+1)

EXAMPLE 27

3-Chloro-N-[1-cyclopentyl-2-(1-isopropylpiperidin-4-yl-methoxy)ethyl]-1H-indole-6-carboxamide Using alkylation method A, 3-chloro-N-[1-cyclopentyl-2-(piperidin-4-ylmethoxy)ethyl]-1H-indole-6-carboxamide (140 mg, 0.35 mmol) and acetone (0.25 mL, 3.5 mmol) afforded, after SCX purification, 67 g (44%) of the title compound.
$^1$H NMR ES-MS m/e 444 (m−1)

EXAMPLE 28

3-Chloro-N-[1-butyl-2-(1-isopropylpiperidin-4-yl-methoxy)-ethyl]-1H-indole-6-carboxamide Using alkylation method A, 3-chloro-N-[1-butyl-2-(piperidin-4-ylmethoxy)ethyl]-1H-indole-6-carboxamide (0.18 mmol) and acetone (1 mL, 14 mmol) afforded, after SCX purification, 60 mg (70%) of the title compound.
$^1$H NMR ES-MS m/e 435 (m+1)

PREPARATION 41

Benzyl N-[(R)-2-(1-Isopropylpiperidin-4-yl-methoxy)-1-phenyl-ethyl]carbamate

Using alkylation method A, benzyl N-[(R)-1-phenyl-2-(piperidin-4-ylmethoxy)ethyl]carbamate hydrochloride (3.7 g, 0.91 mmol) and acetone (2.3 g, 40 mmol) afforded, after purification (SiO2: 8:2:1 hexane:EtOAc:isopropylamine), 1.1 g (29%) of the title compound.
$^1$H NMR ES-MS m/e 411 (m+1)

PREPARATION 42

Benzyl N-[(R)-1-(Isopropyl)-2-(1-isopropylpiperidin-4-yl-methoxy)ethyl]carbamate Using alkylation method A, benzyl N-[(R)-1-(isopropyl)-2-(piperidin-4-ylmethoxy)ethyl]carbamate (1.1 g, 3.2 mmol) and acetone (5 mL, 68 mmol) afforded 1.1 g (92%) of the title compound.
$^1$H NMR ES-MS m/e 377(m+1)

PREPARATION 43

(R)-2-(1-Isopropylpiperidin-4-ylmethoxy)-1-phenyl-ethylamine

Using deprotection method C, keeping the reaction at room temperature, benzyl N-[(R)-2-(1-isopropylpiperidin-4-yl-methoxy)-1-phenylethyl]carbamate (1.5 g, 3.7 mmol) afforded 725 mg (72%) of the title compound.
$^1$H NMR ES-MS m/e 277 (m+1)

PREPARATION 44

(R)-1-(Isopropyl)-2-(1-isopropylpiperidin-4-yl-methoxy)-ethylamine

Using deprotection method A, benzyl N-[(R)-1-(iso-propyl)-2-(1-isopropylpiperidin-4-ylmethoxy)ethyl]carbamate (1.1 g, 3.0 mmol) afforded 541 mg (75%) of the title compound.
$^1$H NMR ES-MS m/e 243 (m+1)

EXAMPLE 29

N-[(R)-2-(1-Isopropylpiperidine-4-ylmethoxy)-1-phenylethyl]-4-methoxybenzamide hydrochloride Using coupling method B, (R)-2-(1-isopropylpiperidin-4-ylmethoxy)-1-phenylethylamine (150 mg, 0.54 mmol) and 4-methoxybenzoyl chloride (0.12 mL, 1.0 mmol) afforded, after purification (SiO2: 4:2:1 DCM:EtOAc:isopropylamine) and conversion to the HCl salt by general method A, 205 mg (91%) of the title compound.
$^1$H NMR ES-MS m/e 411 (m+1)

EXAMPLE 30

4-Chloro-N-[(R)-2-(1-isopropylpiperidine-4-yl-methoxy)-1-phenylethyl]benzamide hydrochloride Using coupling method B, (R)-2-(1-isopropylpiperidin-4-ylmethoxy)-1-phenylethylamine (150 mg, 0.54 mmol) and 4-chlorobenzoyl chloride (0.14 mL, 1.1 mmol) afforded, after purification (SiO2: 4:2:1 DCM:EtOAc:isopropylamine) and conversion to the HCl salt by general method A, 205 mg (87%) of the title compound.
$^1$H NMR ES-MS m/e 415 (m+1)

EXAMPLE 31

N-[(R)-2-(1-Isopropylpiperidine-4-ylmethoxy)-1-phenylethyl]-1H-indole-6-carboxamide hydrochloride Using coupling method A, (R)-2-(1-isopropylpiperidin-4-ylmethoxy)-1-phenylethylamine (200 mg, 0.73 mmol) and indole-6-carboxylic acid (117 mg, 0.73 mmol) afforded, after purification (SiO2: 4:2:1 DCM:EtOAc:isopropylamine) and conversion to the HCl salt by general method A, 270 mg (91%) of the title compound.
$^1$H NMR ES-MS m/e 420 (m+1)

EXAMPLE 32

5-Chloro-N-[(R)-2-(1-isopropylpiperidine-4-yl-methoxy)-1-phenylethyl]-1H-indole-2-carboxamide hydrochloride Using coupling method A, (R)-2-(1-isopropylpiperidin-4-ylmethoxy)-1-phenylethylamine (200 mg, 0.73 mmol) and 5-chloroindole-2-carboxylic acid (142 mg, 0.75 mmol) afforded, after purification (SiO2: 4:2:1 DCM:EtOAc:isopropylamine) and conversion to the HCl salt by general method A, 320 mg (92%) of the title compound.
$^1$H NMR ES-MS m/e 454 (m+1)

EXAMPLE 33

3-Chloro-N-[(R)-1-(Isopropyl)-2-(1-isopropylpiperidine-4-yl-methoxy)ethyl]-1H-indole-6-carboxamide hydrochloride Using coupling method A, (R)-1-(isopropyl)-2-(1-isopropylpiperidin-4-ylmethoxy)ethylamine (135 mg, 0.56 mmol) and 3-chloroindole-6-carboxylic acid (109 mg, 0.56 mmol) afforded, after purification (SiO2: 4:2:1 DCM:EtOAc:isopropylamine) and conversion to the HCl salt by general method A, 167 mg (66%) of the title compound.

$^1$H NMR ES-MS m/e 420 (m+1)

EXAMPLE 34

3-Chloro-N-[(R)-1-phenyl-2-[2-(piperidin-4-yl)ethoxy]ethyl]-1H-indole-6-carboxamide hydrochloride Using deprotection method D, 4-[2-{(R)-2-[(3-chloro-1H-indole-6-carbonyl)amino]-2-phenylethoxy}ethyl]piperidine-1-carboxylic acid tert-butyl ester (474 mg, 0.9 mmol) afforded 394 mg (98%) of the title compound.

$^1$H NMR ES-MS m/e 426 (m+1)

The starting material was prepared as described in Preparations 45 and 46 below.

PREPARATION 45

4-[2-[(R)-2-Amino-2-phenylethoxy]ethyl]piperidine-1-carboxylic acid tert-butyl ester Using amino alkylation method A, substituting 4-(2-methanesulfonyloxyethyl)piperidine-1-carboxylic acid tert-butyl ester for 4-(methanesulfonyloxymethyl)piperidine-1-carboxylic acid tert-butyl ester, (R)-phenylglycinol (2.0 g, 14.6 mmol) afforded, after purification (SiO2: 50 to 100% EtOAc in hexane, 2.5 g (49%) of the title compound.

$^1$H NMR ES-MS m/e 349 (m+1)

PREPARATION 46

4-[2-{(R)-2-[(3-Chloro-1H-indole-6-carbonyl)amino]-2-phenyl-ethoxy}ethyl]piperidine-1-carboxylic acid tert-butyl ester Using coupling method A, 4-[2-[(R)-2-amino-2-phenylethoxy]3 ethyl]piperidine-1-carboxylic acid tert-butyl ester (500 mg, 1.4 mmol) and 3-chloroindole-6-carboxylic acid (280 mg, 1.4 mmol) afforded, after purification (SiO2: 50% EtOAc in hexane), 474 mg (63%) of the title compound.

$^1$H NMR ES-MS m/e 526 (m+1)

EXAMPLE 35

3-Chloro-N-[(R)-1-phenyl-2-[2-(1-methylpiperidin-4-yl)-ethoxy]ethyl]-1H-indole-6-carboxamide hydrochloride Using alkylation method B, 3-chloro-N-[(R)-1-phenyl-2-[2-(piperidin-4-yl)ethoxy]ethyl]-1H-indole-6-carboxamide hydrochloride (300 mg, 0.65 mmol) and paraformaldehyde (195 mg, 6.5 mmol) afforded 213 mg (75%) of the title compound.

$^1$H NMR ES-MS m/e 441 (m+1)

EXAMPLE 36

3-Chloro-N-[(R)-1-phenyl-2-[3-(piperidin-1-yl)propoxy]-ethyl]-1H-indole-6-carboxamide Using coupling method A, (R)-1-phenyl-2-[3-(piperidin-1-yl)propoxy]ethylamine (218 mg, 0.83 mmol) and 3-chloroindole-6-carboxylic acid (179 mg, 0.91 mmol) afforded, after purification (SiO2: 50% EtOAc in hexane), 115 mg (32%) of the title compound.

$^1$H NMR ES-MS m/e 440 (m+1)

The starting material was prepared as described in Preparation 47 below.

PREPARATION 47

(R)-1-Phenyl-2-[3-(piperidin-1-yl)propoxy]ethylamine

Using amino alcohol alkylation method A, substituting 1-(3-chloropropyl)piperidine hydrochloride for 4-(methanesulfonyloxymethyl)piperidine-1-carboxylic acid tert-butyl ester, (R)-phenylglycinol (400 mg, 2.9 mmol) afforded, after purification (SiO2: 8:2:1 hexane:EtOAc:isopropylamine), 220 mg (29%) of the title compound.

$^1$H NMR ES-MS m/e 263 (m+1)

EXAMPLE 37

3-Chloro-N-[4-(1-isopropylpiperidin-4-yl)-1-phenylbutyl]-1H-indole-6-carboxamide Using coupling method A, crude 4-(1-isopropylpiperidin-4-yl)-1-phenylbutylamine hydrochloride (0.70 mmol) and 3-chloroindole-6-carboxylic acid (162 mg, 0.83 mmol) afforded, after purification (SiO2: 10:10:1 hexane:EtOAc:isopropylamine), 66 mg (13%) of the title compound.

$^1$H NMR ES-MS m/e 452 (m+1)

The starting material was prepared as described in Preparations 48 to 53 below.

PREPARATION 48

1-Phenyl-4-(pyridin-4-yl)butan-1-one oxime

To a solution of 1-phenyl-4-(pyridin-4-yl)butan-1-one (2.0 g, 8.7 mmol) in 20 mL of EtOH was added hydroxylamine hydrochloride (0.73 g, 10 mmol) and sodium acetate (1.4 g, 17 mmol). The reaction flask was heated at 80° C. for 4 h and was then cooled to room temperature. Addition of water and filtration of the resultant precipitate afforded 2.0 g (89%) of the title compound.

$^1$H NMR
NMR
ES-MS m/e 241 (m+1)

PREPARATION 49

1-Phenyl-4-(pyridin-4-yl)butylamine

Using deprotection method A under 4.1 bar (60 psig) of hydrogen, 1-phenyl-4-(pyridin-4-yl)butan-1-one oxime (1.6 g, 6.5 mmol) afforded 1.3 g (87%) of the title compound.

$^1$H NMR ES-MS m/e 227 (m+1)

PREPARATION 50

N-[1-Phenyl-4-(pyridin-4-yl)-butyl]carbamic acid tert-butyl ester

Using coupling method B, but substituting triethylamine for pyridine and using THF as solvent, 1-phenyl-4-(pyridin-4-yl)butylamine (1.0 g, 4.5 mmol) and di-tert-butyl dicarbonate (1.5 g, 6.8 mmol) afforded 1.2 g (82%) of the title compound as a crude residue which was used without further purification.

$^1$H NMR ES-MS m/e 227 (m+1)

PREPARATION 51

N-[1-Phenyl-4-(piperidine-4-yl)butyl]carbamic acid tert-butyl ester

Agitating N-[1-phenyl-4-(pyridin-4-yl)butyl]carbamic acid tert-butyl ester (230 mg, 0.70 mmol) and a catalytic amount of platinum oxide in 25 mL of acetic acid under an atmosphere of hydrogen at 4.1 bar (60 psig) afforded, after filtration through diatomaceous earth and removal of solvent under reduced pressure, the title compound as a crude residue that was used without further purification.

$^1$H NMR ES-MS m/e 333 (m+1)

PREPARATION 52

N-[4-(1-Isopropylpiperidin-4-yl)-1-phenylbutyl]carbamic acid tert-butyl ester

Using alkylation method A, crude N-[1-phenyl-4-(piperidine-4-yl)butyl]carbamic acid tert-butyl ester (0.70 mmol) and acetone (1.5 mL, 20 mmol) afforded the title compound as a crude residue that was used without further purification.

$^1$H NMR ES-MS m/e 375 (m+1)

PREPARATION 53

4-(1-Isopropylpiperidin-4-yl)-1-phenylbutylamine hydrochloride

Using deprotection method D, crude N-[4-(1-isopropylpiperidin-4-yl)-1-phenylbutyl]carbamic acid tert-butyl ester (0.70 mmol) afforded 200 mg of the title compound as a crude residue that was used without further purification.

$^1$H NMR ES-MS m/e 275 (m+1)

EXAMPLE 38

3-Chloro-N-[4-(4-isopropylpiperazin-1-yl)-1-phenyl-butyl]-1H-indole-6-carboxamide Using coupling method A, crude 4-(4-isopropylpiperazin-1-yl)-1-phenylbutylamine (530 mg, 1.9 mmol) and 3-chloroindole-6-carboxylic acid (376 mg, 1.9 mmol) afforded, after purification (SiO2: 10:10:1 hexane:EtOAc:isopropylamine), 184 mg (21%) of the title compound.

$^1$H NMR ES-MS m/e 454 (m+1)

The starting material was prepared as described in Preparations 54 to 56 below.

PREPARATION 54

4-Hydroximino-4-phenylbutyric acid

To a solution of 4-oxo-4-phenylbutyric acid (1.0 g, 5.3 mmol) in 50 mL of EtOH was added hydroxylamine hydrochloride (742 mg, 11 mmol) and sodium acetate (1.8 g, 21 mmol). The reaction flask was heated at 80° C. for 4 h and was then cooled to room temperature. Addition of water and filtration of the resultant precipitate afforded, after recrystallization (10:1 chloroform:hexane), 620 mg (60%) of the title compound.

$^1$H NMR ES-MS m/e 192 (m−1)

PREPARATION 55

1-(4-Isopropylpiperazin-1-yl)-4-phenylbutane-1,4-dione 4-oxime

Using coupling method A, 4-hydroximino-4-phenylbutyric acid (500 mg, 2.6 mmol) and 1-isopropylpiperazine dihydrochloride (521 mg, 2.6 mmol) afforded, after purification (SiO2: 10% isopropylamine in EtOAc), 730 mg (89%) of the title compound.

$^1$H NMR

PREPARATION 56

4-(4-Isopropylpiperazin-1-yl)-1-phenyl-butylamine

To a solution of 1-(4-isopropylpiperazin-1-yl)-4-phenylbutane-1,4-dione 4-oxime (625 mg, 2.0 mmol) in 10 mL of THF was slowly added lithium aluminum hydride (250 mg, 6.6 mmol). The reaction flask was heated at 70° C. for 4 h after which time the flask was cooled to 0 C and the reaction was quenched by slow addition of water and 1 N sodium hydroxide. The biphasic mixture was filtered through a pad of diatomaceous earth, and the filtered solution was concentrated to dryness to afford 536 mg (98%) of the title compound as a crude residue that was used without further purification.

$^1$H NMR ES-MS m/e 276 (m+1)

EXAMPLE 39

3-Chloro-N-{(R)-2-[(1-isopropylpiperidin-4-ylmethyl)-(methyl) amino]-1-phenylethyl}-1H-indole-6-carboxamide Using coupling method A, crude (R)-N$^2$-(1-isopropyl-piperidin-4-ylmethyl)-N$^2$-methyl-1-phenylethane-1,2-diamine dihydrochloride (500 mg, 1.4 mmol) and 3-chloroindole-6-carboxylic acid (325 mg, 1.7 mmol) afforded, after purification (SiO2: 0 to 30% isopropylamine in 1:1 hexane: EtOAc), 115 mg (18%) of the title compound.

$^1$H NMR ES-MS m/e 467 (m+1)

The starting material was prepared as described in Preparations 57 to 60 below.

PREPARATION 57

N-[(R)-2-[(1-Isopropylpiperidin-4-ylmethyl)amino]-1-phenyl-2-oxoethyl]carbamic acid tert-butyl ester Using coupling method A, N-Boc-(R)-phenylglycine (3.6 g, 14.5 mmol) and 1-isopropylpiperidin-4-ylmethylamine dihydrochloride (3.3 g, 14.5 mmol) afforded, after purification (SiO2: 0 to 30% isopropylamine in 1:1 hexane:EtOAc), 5.3 g (94%) of the title compound.

$^1$H NMR ES-MS m/e 390 (m+1)

PREPARATION 58

N-[(R)-2-[(1-Isopropylpiperidin-4-ylmethyl)amino]-1-phenyl-ethyl]carbamic acid tert-butyl ester To a solution of N-[(R)-2-[(1-isopropylpiperidin-4-yl-methyl) amino]-1-phenyl-2-oxoethyl]carbamic acid tert-butyl ester (1.0 g, 2.6 mmol) in 15 mL of THF was added 65 wt % sodium bis(2-methoxyethoxy)aluminum hydride in toluene (2.4 mL, 7.7 mmol). The reaction mixture was heated at reflux for 3 h after which time the mixture was cooled to 0° C. and the reaction was quenched by the slow addition of a saturated solution of Rochelle's salt. The product was extracted into EtOAc; and the combined extracts were dried over sodium sulfate, filtered, and concentrated to afford, after purification (SiO2: 0 to 30% isopropylamine in 1:1 hexane:EtOAc), 0.9 g (94%) of the title compound.

$^1$H NMR ES-MS m/e 376 (m+1)

PREPARATION 59

N-[(R)-2-[(1-Isopropylpiperidin-4-ylmethyl)(methyl)amino]-1-phenylethyl]carbamic acid tert-butyl ester Using alkylation method B, N-[(R)-2-[(1-isopropyl-piperidin-4-ylmethyl)amino]-1-phenylethyl]carbamic acid tert-butyl ester (511 mg, 1.4 mmol) and paraformaldehyde (816 mg, 27 mmol) afforded 522 mg (98%) of the title compound as a crude residue that was used without further purification.

$^1$H NMR ES-MS m/e 390 (m+1)

PREPARATION 60

(R)-$N^2$-(1-Isopropylpiperidin-4-ylmethyl)-$N^2$-methyl-1-phenyl-ethane-1,2-diamine hydrochloride Using deprotection method D, crude N-[(R)-2-[(1-iso-propylpiperidin-4-ylmethyl)(methyl)amino]-1-phenylethyl]-carbamic acid tert-butyl ester (522 mg, 1.3 mmol) afforded 600 mg of the title compound as a crude residue that was used without further purification.

$^1$H NMR ES-MS m/e 290 (m+1)

EXAMPLE 40

3-Chloro-N-{(R)-2-[(1-isopropylpiperidin-4-ylmethyl)amino]-1-phenylethyl}-1H-indole-6-carboxamide A solution of N-[(R)-2-(3-chloro-1H-indole-6-carbonyl)-amino-2-phenylethyl]-N-(1-isopropylpiperidin-4-ylmethyl)-carbamic acid 9H-fluoren-9-ylmethyl ester (111 mg, 0.16 mmol) and piperidine (0.08 mL, 0.82 mmol) in 5 mL of DCM was stirred at room temperature for 2 h. Concentration of the reaction mixture afforded, after purification (SiO2: 0 to 30% isopropylamine in 1:1 hexane:EtOAc), 18 mg (23%) of the title compound.

$^1$H NMR ES-MS m/e 453 (m+1)

The starting material was prepared as describe din Preparations 61 to 63 below.

PREPARATION 61

N-[(R)-2-[(9H-Fluoren-9-ylmethoxycarbonyl)(1-isopropyl-piperidin-4-ylmethyl)amino]-1-phenyl-ethyl]carbamic acid tert-butyl ester Using coupling method B, N-[(R)-2-[(1-isopropylpiperidin-4-ylmethyl)amino]-1-phenylethyl]carbamic acid tert-butyl ester (1.1 g, 2.8 mmol) and 9-fluorenylmethyl N-succinimidyl carbonate (Fmoc-OSu, 962 mg, 2.9 mmol) afforded 1.9 g of the title compound as a crude residue, that was used without further purification.

$^1$H NMR ES-MS m/e 598 (m+1)

PREPARATION 62

N-[R)-2-Amino-2-phenylethyl]-N-(1-isopropylpiperidin-4-yl-methyl)carbamic acid 9H-fluoren-9-ylmethyl ester Using deprotection method D, crude N-[(R)-2-[(9H-fluoren-9-ylmethoxycarbonyl)(1-isopropylpiperidin-4-yl-methyl)amino]-1-phenylethyl]carbamic acid tert-butyl ester (1.7 g, 2.8 mmol) afforded 1.0 g (71%) of crude product, that was used without further purification.

$^1$H NMR ES-MS m/e 499 (m+1)

PREPARATION 63

N-[(R)-2-(3-Chloro-1H-indole-6-carbonyl)amino-2-phenyl-ethyl]-N-(1-isopropylpiperidin-4-ylmethyl) carbamic acid 9H-fluoren-9-ylmethyl ester Using coupling method A, crude N-[(R)-2-amino-2-phenyl-ethyl]-N-(1-isopropylpiperidin-4-ylmethyl)carbamic acid 9H-fluoren-9-ylmethyl ester (980 mg, 2.0 mmol) and 3-chloro-indole-6-carboxylic acid (462 mg, 2.4 mmol) afforded, after purification (SiO2: 0 to 30% isopropylamine in 1:1 hexane:EtOAc), 300 mg (23%) of the title compound.

$^1$H NMR ES-MS m/e 675 (m+1)

Assay Protocols

Enzyme Inhibition Assays:

The ability of a test compound to inhibit factor Xa may be evaluated in one or more of the following Enzyme Inhibition assays, or in other standard assays known to those skilled in the art.

Enzyme Inhibition Assay

Human factor Xa and human thrombin are purchased from Enzyme Research Laboratories (South Bend, Ind., USA). Other proteases are from other commercial sources. Chromogenic para-nitroanilide peptide protease substrates are purchased from Midwest Biotech (Fishers, Ind., USA).

The binding affinities for human factor Xa are were measured as apparent association constants (Kass) derived from protease inhibition kinetics as described previously.[a,b,c,d] The apparent Kass values are obtained using automated (BioMek-1000) dilutions of inhibitors (Kass determinations are performed in triplicate at each of four-eight inhibitor concentrations) into 96-well plates and chromogenic substrate hydrolysis rates determined at 405 nm using a Thermomax plate reader from Molecular Devices (San Francisco). For factor Xa inhibition, the assay protocol is: 50 μL buffer (0.06 M tris, 0.3 M NaCl, pH 7.4); 25 μL inhibitor test solution (in MeOH); 25 μL human factor Xa (32 nM in 0.03 M tris, 0.15 M NaCl, 1 mg/mL HSA); finally, 150 μL BzIleGluGlyArgpNA (0.3 mM in water) added within 2 min to start hydrolysis. Final [factor Xa] is 3.2 nM. [Free Xa] and [bound Xa] are determined from linear standard curves on the same plate by use of SoftmaxPro software for each inhibitor concentration and apparent Kass calculated for each inhibitor concentration which produced hydrolysis inhibition between 20% and 80% of the control (3.2 nM factor Xa): apparent Kass=[E:I]/[E$_f$][I$_f$]=[E$_b$]/[E$_f$][I°-I$_b$]. The apparent Kass values so obtained are approximately the inverse of the Ki for the respective inhibitors [1/appKass=app Ki]. The variability of mean apparent Kass values determined at the single substrate concentration is +/−15%. The assay system Km was measured as 0.347+/−0.031 mM [n=4]; and Vmax was 13.11+/−0.76 μM/min.

Kass values are determined with thrombin and other proteases using the same protocol with the following enzyme and substrate concentrations:

thrombin, 5.9 nM with 0.2 mM BzPheValArgpNA;
factor XIa, 1.2 nM with 0.4 mM pyroGluProArgpNA;
factor XIIa, 10 nM with 0.2 mM HDProPheArgpNA;
plasmin, 3.4 nM with 0.5 mM HDValLeuLyspNA;
nt-PA, 1.2 nM with 0.8 mM HDIleProArgpNA;
urokinase, 0.4 nM with 0.4 mM pyroGluGlyArgpNA;
aPC, 3 nM with 0.174 mM pyroGluProArgpNA;
plasma kallikrein, 1.9 nM with D-ProPheArgpNA; and
bovine trypsin, 1.4 nM with 0.18 mM BzPheValArgpNA.

Citations (a) Sall D J, J A Bastian, S L Briggs, J A Buben, N Y Chirgadze, D K Clawson, M L Denny, D D Giera, D S Gifford-Moore, R W Harper, K L Hauser, V J Klimkowski, T J Kohn, H-S Lin, J R McCowan, A D Palkowitz, G F Smith, M E Richett, K Takeuchi, K J Thrasher, J M Tinsley, B G Utterback, S-CB Yan, M Zhang. Dibasic Benzo[b]thiophenes Derivatives as a Novel Class of Active Site Directed Thrombin Inhibitors. 1. Determination of the Serine Protease Selectivity, Structure-Activity Relationships and Binding Orientation. J Med Chem 40 3489-3493 (1997).

(b) Smith G F, T J Craft, D S Gifford-Moore, W J Coffman, K D Kurz, E Roberts, R T Shuman, G E Sandusky, N D Jones, N Chirgadze, and C V Jackson. A Family of Arginal Thrombin Inhibitors Related to Efegatran. Sem. Thrombos. Hemost. 22, 173-183 (1996).

(c) Smith G F, D S Gifford-Moore, T J Craft, N Chirgadze, K J Ruterbories, T D Lindstrom, J H Satterwhite. Efegatran: A New Cardiovascular Anticoagulant. In New Anticoagulants for the Cardiovascular Patient. Ed. R Pifarre. Hanley & Belfus, Inc., Philadelphia (1997) pp 265-300.

(d) Sall D J, D L Bailey, J A Bastian, N Y Chirgadze, A C Clemens-Smith, M L Denney, M J Fisher, D D Geira, D S Gifford-Moore, R W Harper, L M Johnson, V J Klimkowski, T J Kohn, H S Lin, J R McCowan, A D Palkowitz, M E Richett, G F Smith, D W Snyder, K Takeuchi, J E Toth, M Zang. Diamino Benzo[b]thiophene Derivatives as a Novel Class of Active Site Directed Thrombin Inhibitors: 5. Potency, Efficacy and Pharmacokinetic Properties of Modified C-3 Side Chain Derivatives. J. Med. Chem., 43, 649-663 (2000).

The compounds of formula (I) exemplified herein have been found to exhibit a Kass of greater than 1×10$^6$ L/mole in the enzyme inhibition assay.

The ability of a test compound to elongate Partial Thromboplastin Time (Prothrombin Time) may be evaluated in the following test protocols.

Partial Thromboplastin Time (Prothrombin) Test Protocol

Venous blood is collected into 3.2% (0.109 M) trisodium citrate vacutainer tubes at 1 volume of anticoagulant to nine volumes of blood. The blood cells are separated by centrifugation at 700 g for ten minutes to yield plasma, which is frozen at 70° C. until required.

To perform the test, 100 μL of plasma are pipetted into in a glass test tube, 1 μL of test compound in DMSO is added, and allowed to warm to 37° over two minutes. 100 μL of warm (37°) Manchester (tissue thromboplastin) reagent (Helena Biosciences, UK) is added, allowed to equilibrate for two minutes. 100 μL of warm (37°) 25 mM calcium chloride solution is added to initiate clotting. The test tube is tilted three times through a 90° angle every five seconds to mix the reagents and the time to clot formation recorded. Data from a series of observations and test compound concentrations are analysed by a SAS statistical analysis program and a CT2 (Concentration required to double clotting time) for each compound is generated.

The compounds of the invention have been found to significantly elongate the partial thromboplastin time (Prothrombin time).

Alternative Prothrombin Time and APTT Protocols

Coagulation Determinations: Prothrombin Times and APTT values are determined in HUMAN PLASMA with a STA instrument (Stago). BioPT is a special non-plasma clotting assay triggered with human tissue factor (Innovin). Possible binding to albumen or to lipid are assessed by comparing the BioPT effects in the presence/absence of 30 mg/mL human albumen (HSA) and 1 mg/mL phosphatidyl choline (PC). Inhibitors are delivered in 50% aqueous methanol vehicle.

APTT Assay

75 μL plasma Citrol Baxter-Dade Citrated Normal Human Plasma
25 μL test solution
75 μL Actin Baxter-Dade Activated Cephaloplastin incubate 2 min min. @ 37° C.
75 μl CaCl$_2$ (0.02 M)

PT Assay

75 μL plasma
25 μL test solution
75 μL saline incubate 1 min. @ 37° C.
75 μL Innovin Baxter-Dade Recombinant Human Tissue Factor Further advantageous properties of compounds of formula (I) may be demonstrated by measuring their pharmacodynamic (PD) and pharmacokinetic (PK) properties in laboratory animal species such as rats and dogs following oral dosing in the fasted and in the fed state.

The invention claimed is:

1. A compound of formula (I)

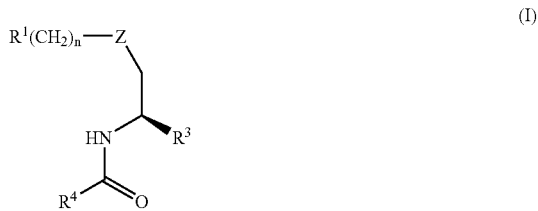

in which:

R$^1$ represents a group of formula

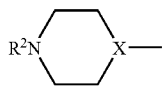

in which X represents CH;

R$^2$ represents a hydrogen atom or a (1-6C)alkyl, (3-6C)cycloalkyl, fluoro(1-4C)alkyl, fluoro(2-4C)alkanoyl, hydroxy(2-4C)alkyl or pyridyl group;

n represents 1, 2 or 3;

Z represents CH$_2$, O or NR$^5$, in which R$^5$ represents a hydrogen atom or a (1-4C)alkyl group;

R$^3$ represents:

(i) phenyl which is unsubstituted or substituted by methylenedioxy or by a substituent selected from halogen, (1-4C)alkyl, hydroxy, (1-4C)alkoxy, trifluoromethyl, difluoromethoxy, trifluoromethoxy, (1-4C)alkylthio, (1-4C)alkylsulfinyl, (1-4C)alkylsulfonyl, carboxy, aminocarbonyl, amino, (2-4C)alkanoylamino, aminosulfonyl, (1-4C)alkylaminosulfonyl, nitro, phenyl, phenoxy, benzyloxy and pyridyl;

(ii) pyridyl, pyrimidyl or pyridazinyl, which is unsubstituted or substituted by a halogen atom;

(iii) furyl, thienyl, imidazolyl, thiazolyl, isothiazolyl, oxazolyl, isoxazolyl, thiadiazolyl, each of which is unsubstituted or substituted by (1-4C)alkyl or amino;

(iv) naphthyl, benzofuryl, benzothienyl, quinolyl or isoquinolyl;

(v) (3-6C)cycloalkyl;

(vi) piperidinyl or tetrahydropyranyl; or (vii) (1-4C)alkyl, which is unsubstituted or substituted by hydroxy, (1-4C)alkoxy, phenoxy, carboxy, aminocarbonyl, aminosulfonyl, (1-4C)alkylthio, phenylthio, pyridylthio, amino, (1-4C)alkylamino, di(1-4C)alkylamino, piperidin-1-yl, morpholino, trifluoromethyl, phenyl, imidazolyl, pyridyl, (3-6C)cycloalkyl, oxa(4-6C)cycloalkyl, or aza(4-6C)cycloalkyl (which may bear an N-(1-4C)alkyl substituent); and R$^4$ is selected from

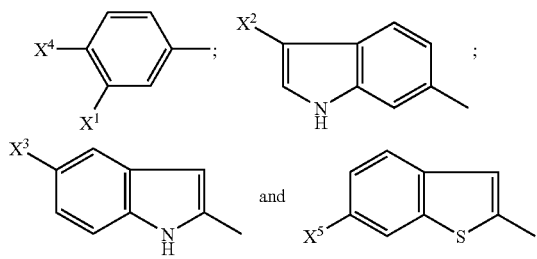

in which

X$^1$ represents a hydrogen atom, a halogen atom or an amino group;

X$^2$ represents a hydrogen atom, a methyl group, a chlorine atom or a bromine atom;

X$^3$ represents a hydrogen atom, a methyl group or a halogen atom;

X$^4$ represents a chlorine atom, a methoxy group or a methyl group; and

X$^5$ represents a hydrogen atom, a halogen atom or a methyl group;

or a pharmaceutically acceptable salt thereof.

2. A compound as claimed in claim 1, in which R$^2$ represents a (1-6C)alkyl, (3-6C)cycloalkyl, fluoro(1-4C)alkyl, fluoro(2-4C)alkanoyl, hydroxy(2-4C)alkyl or pyridyl group.

3. A compound as claimed in claim 2, in which R$^2$ represents a methyl, ethyl, isopropyl, cyclopropyl, cyclopentyl, 2-fluoroethyl, 2,2,2-trifluoroethyl, trifluoroacetyl, 2-hydroxyethyl or pyrid-4-yl group.

4. A compound as claimed in claim 3, in which R$^2$ represents an isopropyl, cyclopropyl, cyclopentyl or pyrid-4-yl group.

5. A compound as claimed in claim 1, in which n represents 1 or 2.

6. A compound as claimed in claim 5, in which n represents 1.

7. A compound as claimed claim 1, in which Z represents CH$_2$.

8. A compound as claimed in claim 1, in which Z represents O.

9. A compound as claimed in claim 1, in which Z represents NR$^5$.

10. A compound as claimed in claim 9, in which R$^5$ is hydrogen.

11. A compound as claimed in claim 1, in which R$^3$ represents:

(i) phenyl, 2,3-methylenedioxyphenyl, 2-fluorophenyl, 4-fluorophenyl, 2-chlorophenyl, 2-methylphenyl, 2-methoxyphenyl, 2-trifluoromethylphenyl, 2-difluoromethoxyphenyl, 4-carboxyphenyl or 4-aminocarbonylphenyl;

(ii) pyrid-2-yl or pyrid-4-yl;

(iii) fur-2-yl, fur-3-yl, thien-2-yl, thien-3-yl, imidazol-2-yl, thiazol-2-yl, thiazol-4-yl, 2-methylthiazol-4-yl or 2-aminothiazol-4-yl;

(iv) naphth-1-yl, naphth-2-yl, benzofuryl, benzothienyl, quinolin-4-yl or quinolin-8-yl;

(v) cyclopropyl, cyclobutyl, cyclopentyl or cyclohexyl; or (vi) methyl, ethyl, propyl, isopropyl, butyl, 2-methylpropyl, hydroxymethyl, 1-hydroxyethyl, methoxymethyl, 1-methoxyethyl, methylthiomethyl, 2-methylthioethyl, prop-2-ylthiomethyl, N,N-dimethylaminomethyl, phenylthiomethyl, pyrid-2-ylthiomethyl, carboxymethyl, 2-carboxyethyl, aminocarbonylmethyl, 2-aminocarbonylethyl, morpholinomethyl, 2,2,2-trifluoroethyl, benzyl, pyrid-2-ylmethyl, pyrid-3-ylmethyl, pyrid-4-yl-methyl, imidazol-1-ylmethyl, imidazol-4-ylmethyl, 3-methylimidazol-4-ylmethyl, cyclohexyl-4-ylmethyl, tetrahydropyran-4-ylmethyl, piperidin-1-ylmethyl or 1-methylpiperidin-4-ylmethyl.

12. A compound as claimed in claim 11, in which R$^3$ represents phenyl, 2-fluorophenyl or 2-chlorophenyl.

13. A compound as claimed in claim 12, in which R$^3$ represents phenyl.

14. A compound as claimed in claim 1, in which R$^4$ is 4-chlorophenyl, 4-methoxyphenyl, indol-6-yl, 3-methylindol-6-yl, 3-chloroindol-6-yl, 5-chloroindol-2-yl or 6-chlorobenzo[b]thiophen-2-yl.

15. A compound as claimed in claim 14, in which R$^4$ is 4-methoxyphenyl, indol-6-yl or 5-chloroindol-2-yl.

16. A pharmaceutical composition, which comprises a compound as claimed in claim 1, together with a pharmaceutically acceptable diluent or carrier.

17. A process for preparing a compound as claimed in claim 1, which comprises
(a) reacting a compound of formula (II)

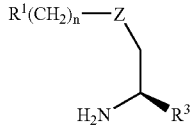
(II)

or a salt thereof, with a compound of formula (III)

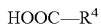
(III)

or a reactive derivative thereof;
(b) for a compound of formula I in which $R^2$ represents a (1-6C)alkyl, (3-6C)cycloalkyl, fluoro(1-4C)alkyl, fluoro(2-4C)alkanoyl or hydroxy(2-4C)alkyl, reacting a corresponding compound of formula (I) in which $R^2$ represents a hydrogen atom, or a salt thereof, with an alkylating or acylating agent;
(c) for a compound of formula (I) in which Z represents NH, deprotecting a compound of formula

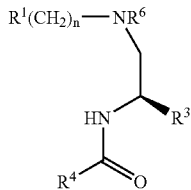
(IV)

in which $R^6$ represents an amino protecting group; or
(d) for a compound of formula (I) in which $R^2$ represents a hydrogen atom, deprotecting a compound of formula (I) in which $R^2$ represents a protecting group;
followed, if a pharmaceutically acceptable salt is desired, by forming a pharmaceutically acceptable salt.
wherein, unless otherwised defined,
$R^1$ represents a group of formula

in which X represents CH;
$R^2$ represents a hydrogen atom or a (1-6C)alkyl, (3-6C) cycloalkyl, fluoro(1-4C)alkyl, fluoro(2-4C)alkanoyl, hydroxy(2-4C)alkyl or pyridyl group;
n represents 1, 2 or 3;
Z represents $CH_2$, O or $NR^5$, in which $R^5$ represents a hydrogen atom or a (1-4C)alkyl group;
$R^3$ represents:
(i) phenyl which is unsubstituted or substituted by methylenedioxy or by a substituent selected from halogen, (1-4C)alkyl, hydroxy, (1-4C)alkoxy, trifluoromethyl, difluoromethoxy, trifluoromethoxy, (1-4C)alkylthio, (1-4C)alkylsulfinyl, (1-4C)alkylsulfonyl, carboxy, aminocarbonyl, amino, (2-4C)alkanoylamino, aminosulfonyl, (1-4C)alkylaminosulfonyl, nitro, phenyl, phenoxy, benzyloxy and pyridyl;

(ii) pyridyl, pyrimidyl or pyridazinyl, which is unsubstituted or substituted by a halogen atom;
(iii) furyl, thienyl, imidazolyl, thiazolyl, isothiazolyl, oxazolyl, isoxazolyl, thiadiazolyl, each of which is unsubstituted or substituted by (1-4C)alkyl or amino;
(iv) naphthyl, benzofuryl, benzothienyl, quinolyl or isoquinolyl;
(v) (3-6C)cycloalkyl;
(vi) piperidinyl or tetrahydropyranyl; or
(vii) (1-4C)alkyl, which is unsubstituted or substituted by hydroxy, (1-4C)alkoxy, phenoxy, carboxy, aminocarbonyl, aminosulfonyl, (1-4C)alkylthio, phenylthio, pyridylthio, amino, (1-4C)alkylamino, di(1-4C)alkylamino, piperidin-1-yl, morpholino, trifluoromethyl, phenyl, imidazolyl, pyridyl, (3-6C)cycloalkyl, oxa(4-6C)cycloalkyl, or aza(4-6C)cycloalkyl (which may bear an N-(1-4C)alkyl substituent); and
$R^4$ is selected from

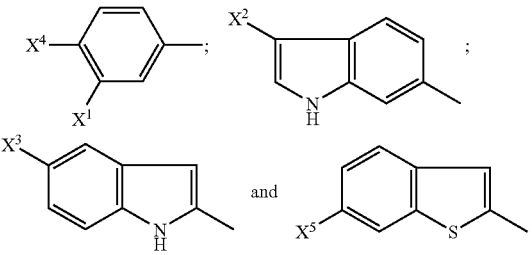

in which
$X^1$ represents a hydrogen atom, a halogen atom or an amino group;
$X^2$ represents a hydrogen atom, a methyl group, a chlorine atom or a bromine atom;
$X^3$ represents a hydrogen atom, a methyl group or a halogen atom;
$X^4$ represents a chlorine atom, a methoxy group or a methyl group; and
$X^5$ represents a hydrogen atom, a halogen atom or a methyl group.

18. A compound of formula (II)

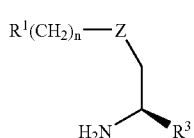
(II)

or a salt thereof, in which
$R^1$ represents a group of formula

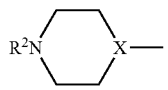

in which X represents CH;
$R^2$ represents a hydrogen atom or a (1-6C)alkyl, (3-6C) cycloalkyl, fluoro(1-4C)alkyl, fluoro(2-4C)alkanoyl, hydroxy(2-4C)alkyl or pyridyl group;
n represents 1, 2 or 3;

Z represents CH$_2$, O or NR$^5$, in which R$^5$ represents a hydrogen atom or a (1-4C)alkyl group; and R$^3$ represents:
(i) phenyl which is unsubstituted or substituted by methylenedioxy or by a substituent selected from halogen, (1-4C)alkyl, hydroxy, (1-4C)alkoxy, trifluoromethyl, difluoromethoxy, trifluoromethoxy, (1-4C)alkylthio, (1-4C)alkylsulfinyl, (1-4C)alkylsulfonyl, carboxy, aminocarbonyl, amino, (2-4C)alkanoylamino, aminosulfonyl, (1-4C)alkylaminosulfonyl, nitro, phenyl, phenoxy, benzyloxy and pyridyl;
(ii) pyridyl, pyrimidyl or pyridazinyl, which is unsubstituted or substituted by a halogen atom;
(iii) furyl, thienyl, imidazolyl, thiazolyl, isothiazolyl, oxazolyl, isoxazolyl, thiadiazolyl, each of which is unsubstituted or substituted by (1-4C)alkyl or amino;
(iv) naphthyl, benzofuryl, benzothienyl, quinolyl or isoquinolyl;
(v) (3-6C)cycloalkyl;
(vi) piperidinyl or tetrahydropyranyl; or
(vii) (1-4C)alkyl, which is unsubstituted or substituted by hydroxy, (1-4C)alkoxy, phenoxy, carboxy, aminocarbonyl, aminosulfonyl, (1-4C)alkylthio, phenylthio, pyridylthio, amino, (1-4C)alkylamino, di(1-4C)alkylamino, piperidin-1-yl, morpholino, trifluoromethyl, phenyl, imidazolyl, pyridyl, (3-6C)cycloalkyl, oxa(4-6C)cycloalkyl, or aza(4-6C)cycloalkyl (which may bear an N-(1-4C)alkyl substituent).

19. A compound of formula (IV)

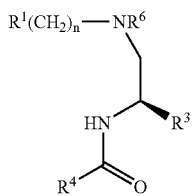

(IV)

or a salt thereof, in which R$^6$ represents an amino protecting group, and

R$^1$ represents a group of formula

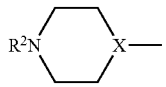

in which X represents CH;

R$^2$ represents a hydrogen atom or a (1-6C)alkyl, (3-6C)cycloalkyl, fluoro(1-4C)alkyl, fluoro(2-4C)alkanoyl, hydroxy(2-4C)alkyl or pyridyl group;

n represents 1, 2 or 3;

R$^3$ represents;
(i) phenyl which is unsubstituted or substituted by methylenedioxy or by a substituent selected from halogen, (1-4C)alkyl, hydroxy, (1-4C)alkoxy, trifluoromethyl, difluoromethoxy, trifluoromethoxy, (1-4C)alkylthio, (1-4C)alkylsulfinyl, (1-4C)alkylsulfonyl, carboxy, aminocarbonyl, amino, (2-4C)alkanoylamino, aminosulfonyl, (1-4C)alkylaminosulfonyl, nitro, phenyl, phenoxy, benzyloxy and pyridyl;
(ii) pyridyl, pyrimidyl or pyridazinyl, which is unsubstituted or substituted by a halogen atom;
(iii) furyl, thienyl, imidazolyl, thiazolyl, isothiazolyl, oxazolyl, isoxazolyl, thiadiazolyl, each of which is unsubstituted or substituted by (1-4C)alkyl or amino;
(iv) naphthyl, benzofuryl, benzothienyl, quinolyl or isoquinolyl;
(v) (3-6C)cycloalkyl;
(vi) piperidinyl or tetrahydropyranyl; or
(vii) (1-4C)alkyl, which is unsubstituted or substituted by hydroxy, (1-4C)alkoxy, phenoxy, carboxy, aminocarbonyl, aminosulfonyl, (1-4C)alkylthio, phenylthio, pyridylthio, amino, (1-4C)alkylamino, di(1-4C)alkylamino, piperidin-1-yl, morpholino, trifluoromethyl, phenyl, imidazolyl, pyridyl, (3-6C)cycloalkyl, oxa(4-6C)cycloalkyl, or aza(4-6C)cycloalkyl (which may bear an N-(1-4C)alkyl substituent); and R$^4$ is selected from

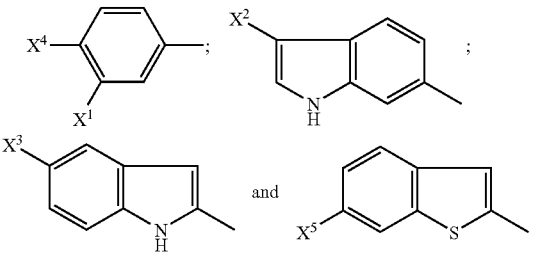

in which
X$^1$ represents a hydrogen atom, a halogen atom or an amino group;
X$^2$ represents a hydrogen atom, a methyl group, a chlorine atom or a bromine atom;
X$^3$ represents a hydrogen atom, a methyl group or a halogen atom;
X$^4$ represents a chlorine atom, a methoxy group or a methyl group; and
X$^5$ represents a hydrogen atom, a halogen atom or a methyl group.

20. A method of treating a thrombotic disorder selected from venous thrombosis, pulmonary thrombosis, arterial thrombosis, myocardial ischaemia, myocardial infarction and cerebral thrombosis in a mammal requiring treatment, which comprises administering an effective amount of a compound as claimed in claim 1.

21. A compound as claimed in claim 1 which is 3-chloro-N—[(R)-1-phenyl-2-(1-isopropylpiperidin-4-ylmethoxy)ethyl]-1H-indole-6-carboxamide, or a pharmaceutically acceptable salt thereof.

* * * * *